US012714387B2

(12) United States Patent
Asanoi

(10) Patent No.: US 12,714,387 B2
(45) Date of Patent: Aug. 25, 2026

(54) HEART SOUND ANALYSIS DEVICE, HEART SOUND ANALYSIS PROGRAM, AND RECORDING MEDIUM

(71) Applicants: Hidetsugu Asanoi, Imizu (JP); HEARTLAB, INC., Kobe (JP)

(72) Inventor: Hidetsugu Asanoi, Imizu (JP)

(73) Assignees: Hidetsugu Asanoi, Imizu (JP); HEARTLAB, INC., Kobe (JP)

( * ) Notice: Subject to any disclaimer, the term of this patent is extended or adjusted under 35 U.S.C. 154(b) by 184 days.

(21) Appl. No.: 18/834,815

(22) PCT Filed: Nov. 24, 2022

(86) PCT No.: PCT/JP2022/043271
§ 371 (c)(1),
(2) Date: Jul. 31, 2024

(87) PCT Pub. No.: WO2023/149058
PCT Pub. Date: Aug. 10, 2023

(65) Prior Publication Data

US 2025/0107771 A1 Apr. 3, 2025

(30) Foreign Application Priority Data

Feb. 1, 2022 (JP) ................................ 2022-014108

(51) Int. Cl.
*A61B 7/04* (2006.01)
*A61B 5/00* (2006.01)

(52) U.S. Cl.
CPC .............. *A61B 7/04* (2013.01); *A61B 5/7275* (2013.01)

(58) Field of Classification Search
None
See application file for complete search history.

(56) References Cited

U.S. PATENT DOCUMENTS 7,930,886 B2 4/2011 Shute
2003/0229289 A1* 12/2003 Mohler ................. A61B 5/318 600/508

(Continued)

FOREIGN PATENT DOCUMENTS

EP 4154805 B1 7/2024
JP 2004529720 A 9/2004

(Continued)

OTHER PUBLICATIONS

Muro, "Auscultation—Sounds III and IV—Trackingauscultatory findings to understand pathological changes," online, May 2013, Medical Tribune, 2 pages with English translation. internet, URL:https://midori-hp.or.jp/wp/wp-content/uploads/2015/08/Medical-Tribune201305.pdf.

(Continued)

*Primary Examiner* — James B Hull
(74) *Attorney, Agent, or Firm* — MH2 Technology Law Group, LLP

(57) ABSTRACT

A heart sound analysis device 3 that analyzes a heart sound signal acquired from a subject comprises an amplitude variation waveform generation unit 33*a* that generates an amplitude variation waveform of the heart sound signal; a peak detection unit 33*b* that detects maximum peaks in the amplitude variation waveform; a time interval calculation unit 33*c* that calculates time intervals between the maximum peaks; and a prediction support unit 33*d* that supports the prediction of the state of the subject based on the time intervals.

5 Claims, 33 Drawing Sheets

(56) References Cited

U.S. PATENT DOCUMENTS

| | | | | |
|---|---|---|---|---|
| 2004/0138572 | A1* | 7/2004 | Thiagarajan | A61B 7/04 600/508 |
| 2007/0118054 | A1 | 5/2007 | Pinhas | |
| 2009/0054792 | A1 | 2/2009 | Sato | |
| 2011/0257548 | A1* | 10/2011 | Dong | A61B 7/04 600/528 |
| 2012/0125337 | A1 | 5/2012 | Asanoi | |
| 2017/0035303 | A1 | 2/2017 | Sullivan et al. | |
| 2019/0313943 | A1 | 10/2019 | Ogawa | |
| 2020/0077913 | A1 | 3/2020 | Shutte et al. | |
| 2022/0142507 | A1 | 5/2022 | Takahashi et al. | |

FOREIGN PATENT DOCUMENTS

| | | | |
|---|---|---|---|
| JP | 2012513858 | A | 6/2012 |
| JP | 2013034670 | A | 2/2013 |
| JP | 2017500998 | A | 1/2017 |
| JP | 2018102736 | A | 7/2018 |
| JP | 2020075136 | A | 5/2020 |
| WO | 2011019091 | A | 2/2011 |
| WO | 2021111680 | A | 6/2021 |

OTHER PUBLICATIONS

International Search Report dated Feb. 14, 2023 for corresponding International Application No. PCT/JP2022/043269, with English translation, 5 pages.

International Search Report dated Feb. 14, 2023 for corresponding International Application No. PCT/JP2022/043271, with English translation, 5 pages.

Search Report dated Apr. 1, 2025 for corresponding European Application No. 22924963.6, 8 pages.

Office Action dated May 5, 2026 for U.S. Appl. No. 18/834,486, 27 pages.

* cited by examiner (a)

(b)

(a)

(b)

Fig. 10
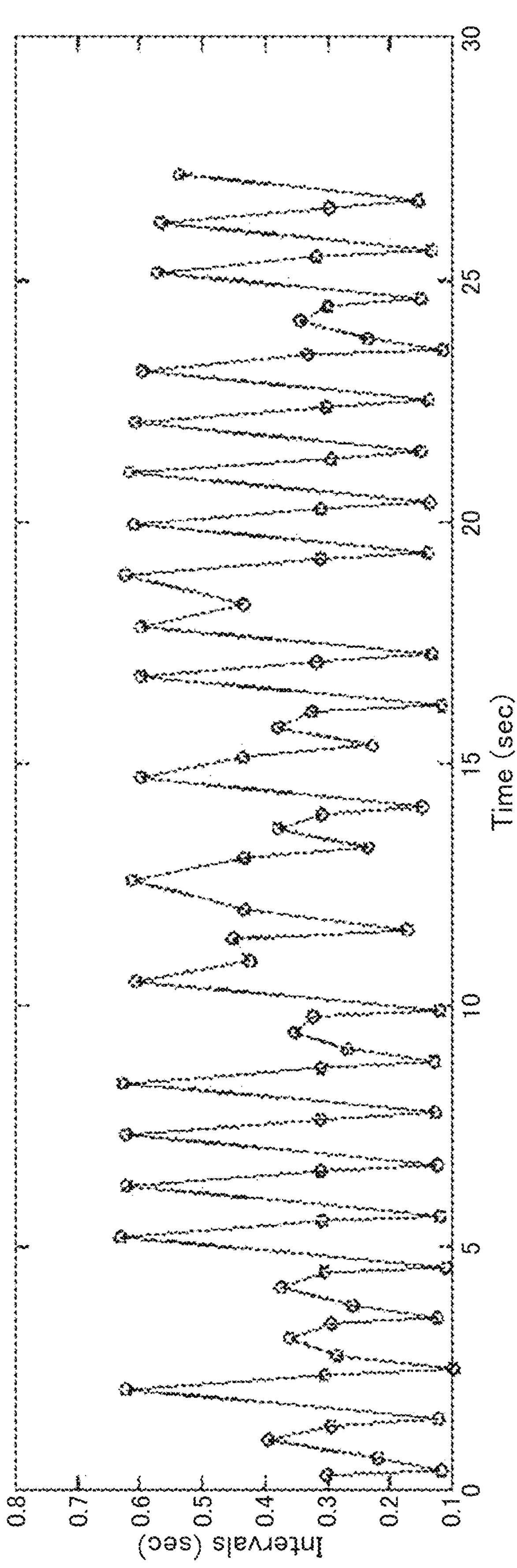
Intervals (sec)
0.8
0.7
0.6
0.5
0.4
0.3
0.2
0.1
0
5
10
15
20
25
30
Time (sec)

DminHBampSD: Each sound intervals (sec)

Sound intervals (sec)

Time(sec)

Fig. 25
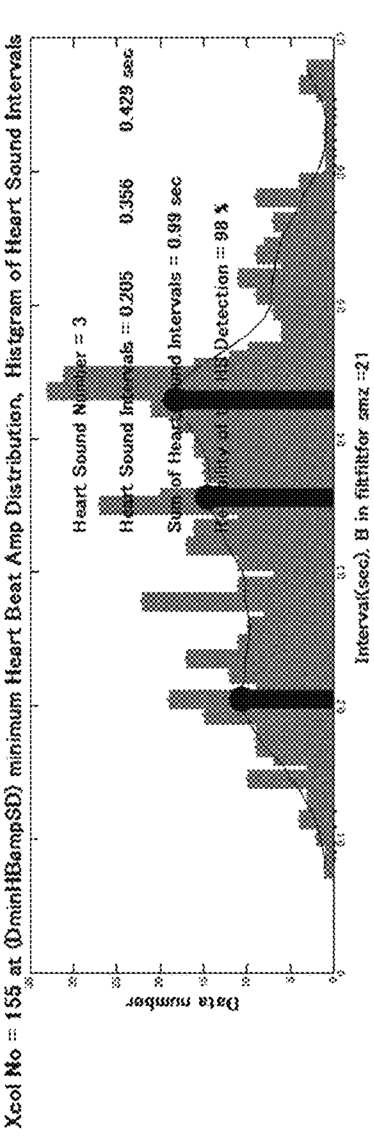

Fig. 27

DminHBIntSD: Heart Sound Peak Locations, FileN=Case 1

Time(sec)

Fig. 28

Time(sec)

Sound intervals (sec)

Fig. 29
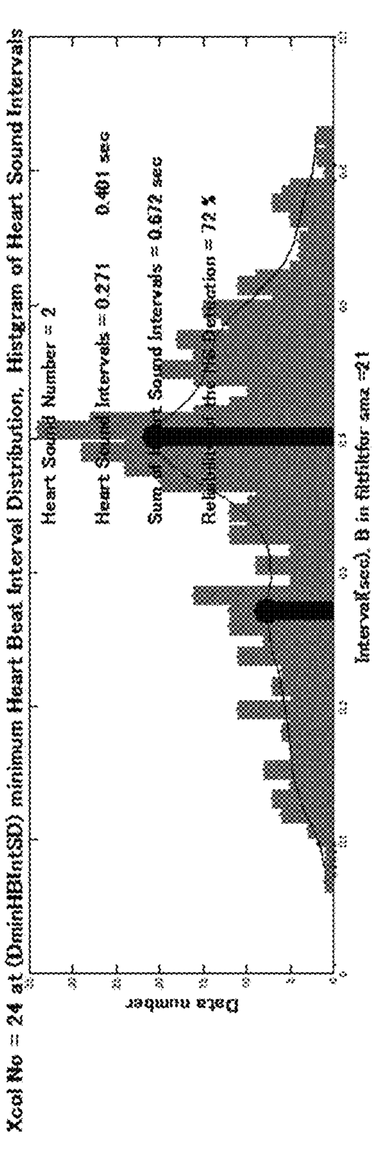

Fig. 33
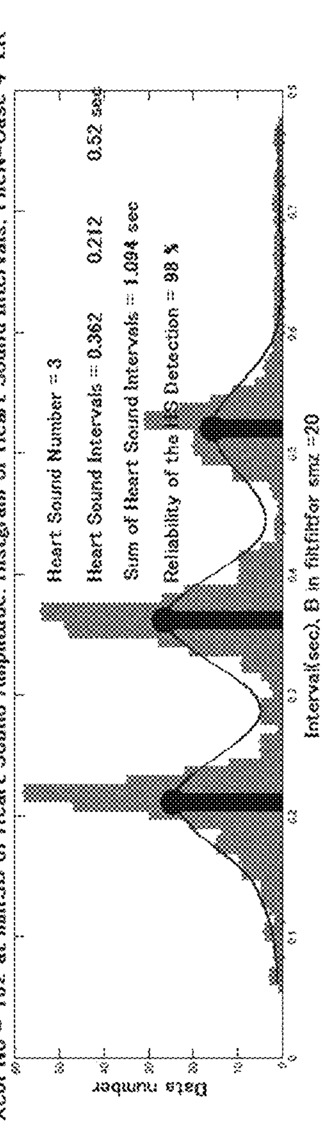

HEART SOUND ANALYSIS DEVICE, HEART SOUND ANALYSIS PROGRAM, AND RECORDING MEDIUM

CROSS-REFERENCE TO RELATED APPLICATIONS

This application is a U.S. national stage application of PCT/JP2022/043271 filed 24 Nov. 2022, which claims the benefit of, and relies on the filing date of, Japanese Patent Application No. 2022-014108 filed 1 Feb. 2022, the entire disclosure of which is incorporated herein by reference.

TECHNICAL FIELD

The present invention relates to a technology for analyzing a heart sound signal acquired from a subject.

BACKGROUND ART

Heart sounds are made by the valves, myocardium, blood flow, etc. when the heart contracts and expands, and are classified into sounds I to IV.

Sound I occurs during ventricular contraction, and mainly includes mitral valve closure sound and aortic valve opening sound. Sound II occurs at the beginning of ventricular diastole, and mainly includes aortic valve closure sound and pulmonary valve closure sound. Sound III occurs after sound II, i.e., during the rapid filling period of the ventricles in early diastole, and is caused by the sudden blockage of blood flow from the atria to the ventricles by the ventricular wall. The more sudden the blockage, the louder the sound, and the sound is likely to occur due to a decrease in ventricular compliance during diastole. Sound IV is caused by the sudden blockage of blood flow ejected into the ventricle by atrial contraction by the ventricular wall during the rise in ventricular end-diastolic pressure just before sound I.

In a healthy adult, generally only sounds I and II can be heard, and sounds III and IV are not confirmed. That is, sounds III and IV are treated as extra heart sounds. If these sounds are confirmed, there may be some kind of disease in the heart.

For example, sound III is heard in mitral regurgitation, aortic regurgitation, ventricular septal defect, myocardial infarction, ischemic heart disease, cardiomyopathy, myocarditis, and the like, and is particularly so important in heart failure that it is used as a sign of congestion to determine hospital admission and discharge. Sound IV is heard in pulmonary hypertension, aortic stenosis, ischemic heart disease, myocarditis, cardiomyopathy, and the like (NPL 1).

CITATION LIST

Non-Patent Literature

NPL 1: Takashi MURO, "Auscultation—Sounds III and IV—Tracking auscultatory findings to understand pathological changes," online, May 2013, Medical Tribune, internet, URL: https://midori-hp.or.jp/wp/wp-content/uploads/2015/08/Medical-Tribune201305.pdf

SUMMARY OF INVENTION

Technical Problem

Since sounds III and IV differ in the mechanism of occurrence from sounds I and II, it takes skill to correctly determine the presence or absence of these sounds even when listening with a stethoscope. However, extra heart sounds are very important findings because they occur or increase when the diseases described in paragraph [0005] are developed or exacerbated. In order to identify sounds I, II, III, and IV on the phonocardiogram, information on the systolic and diastolic phases of the heart is necessary, which requires simultaneous measurement of the electrocardiogram, which requires the attachment of a sensor.

The present invention was made to solve the above problems, and an object thereof is to analyze a heart sound signal acquired from a subject, thereby supporting the prediction of the subject's state.

Solution to Problem

In order to achieve the above object, the present invention includes the following aspects.

Item 1

A heart sound analysis device that analyzes a heart sound signal acquired from a subject, comprising:

- an amplitude variation waveform generation unit that generates an amplitude variation waveform of the heart sound signal;
- a peak detection unit that detects maximum peaks in the amplitude variation waveform;
- a time interval calculation unit that calculates time intervals between the maximum peaks; and
- a prediction support unit that supports the prediction of the state of the subject based on the time intervals.

Item 2

The heart sound analysis device according to Item 1, wherein the prediction support unit comprises a distribution information generation unit that generates distribution information indicating the distribution of the time intervals.

Item 3

The heart sound analysis device according to Item 2, wherein the distribution information generation unit generates the distribution information in a histogram format.

Item 4

The heart sound analysis device according to any one of Items 1 to 3, wherein the prediction support unit comprises an extra heart sound identification unit that identifies the presence or absence of extra heart sounds in the heart sound signal and the type of extra heart sound based on the time intervals.

Item 5

The heart sound analysis device according to Item 4, wherein when nth peak in the amplitude variation waveform is taken as Pn, and the time interval between (n−1)th peak Pn−1 and the nth peak Pn is taken as Sn, the extra heart sound identification unit

- searches maximum peaks that satisfy $S_{n-1} < S_n > S_{n+1}$, and minimum peaks that satisfy $S_{n-1} > S_n < S_{n+1}$,
- selects any maximum peak as a first peak from the searched maximum peaks, selects a minimum peak immediately following the first peak as a second peak, and selects a maximum peak immediately following the second peak as a third peak, calculates a ratio of the time interval between the second and third peaks to the time interval between the first and second peaks, and determines the identification based on the ratio.

Item 6

A heart sound analysis program for making a computer work as each unit of the heart sound analysis device according to any one of Items 1 to 5.

Item 7

A computer-readable recoding medium that records the heart sound analysis program according to Item 6.

Advantageous Effects of Invention

The present invention can analyze a heart sound signal acquired from a subject, thereby supporting the prediction of the subject's state.

BRIEF DESCRIPTION OF DRAWINGS

FIG. 10 shows an example of distribution information of peak time intervals detected from the amplitude variation waveform.

FIG. 14 is a graph plotting peaks of the amplitude variation waveform of the heart sound signal including sound IV, with the time on the x-axis and the time interval with the immediately preceding peak on the y-axis.

FIG. 17 shows the amplitude variation waveform of the heart sound signal shown in FIG. 16.

FIG. 24 shows distribution information of peak time intervals detected from the amplitude variation waveform shown in FIG. 23.

FIG. 25 shows the distribution information shown in FIG. 24 in a histogram format.

FIG. 27 shows the amplitude variation waveform of the heart sound signal shown in FIG. 26.

FIG. 28 shows distribution information of peak time intervals detected from the amplitude variation waveform shown in FIG. 27. FIG. 27.

FIG. 29 shows the distribution information shown in FIG. 28 in a histogram format.

FIG. 33 shows the histogram of the distribution of peak time intervals detected from the amplitude variation waveform of the heart sound signal shown in FIG. 32.

DESCRIPTION OF EMBODIMENTS

An embodiment of the present invention is described below with reference to the attached drawings. The present invention is not limited to the following embodiment.

System Structure

Figure 1:
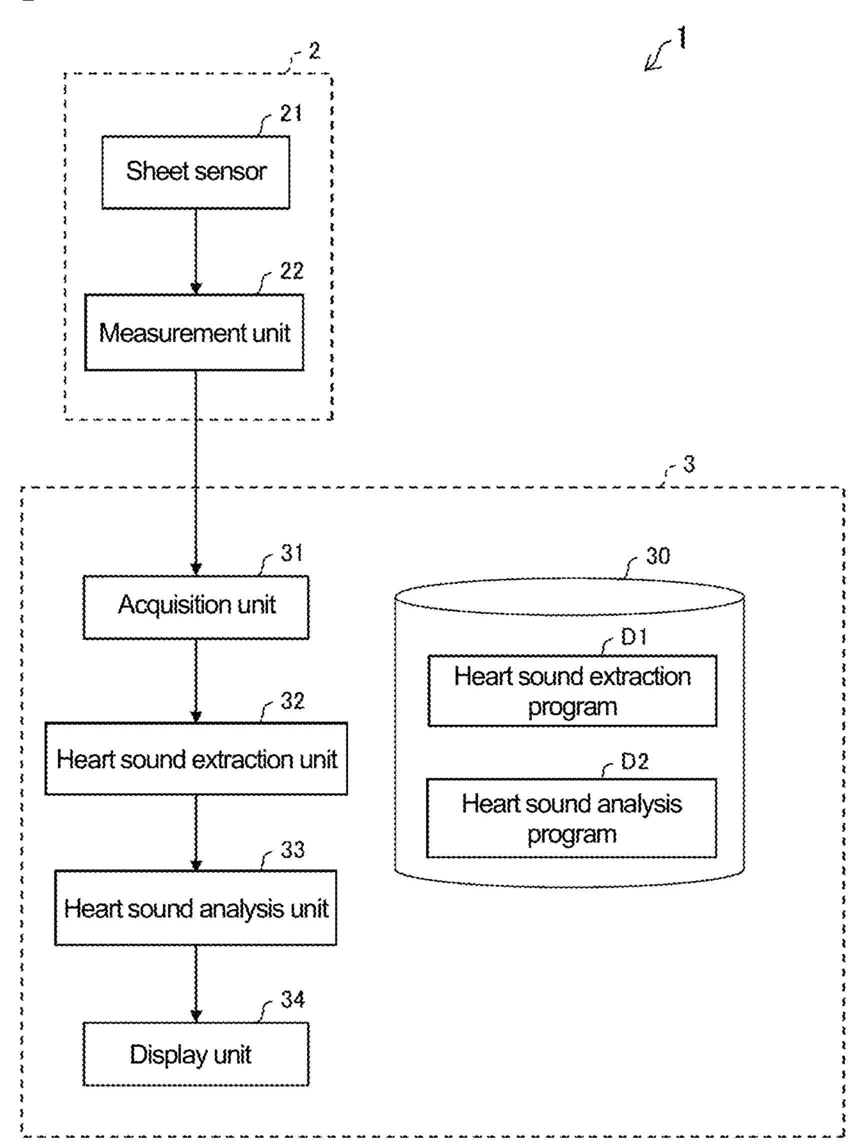
FIG. 1 is a block diagram showing the schematic structure of a monitoring system according to an embodiment of the present invention.

FIG. 1 is a block diagram showing the schematic structure of a monitoring system 1 according to an embodiment of the present invention. The monitoring system 1 monitors the state of a subject based on the heart sounds of the subject, and comprises a measuring device 2 and a management device 3. The subject targeted in the present embodiment is mainly a patient with heart disease staying in a place other than a medical institution, such as home; however, the place where the subject stays is not particularly limited. In addition, in the present embodiment, the disease of the subject is a disease that can be diagnosed or predicted from the heart sounds; however, it is not necessary to particularly limit the disease, and the subject may be a healthy person.

Figure 2:
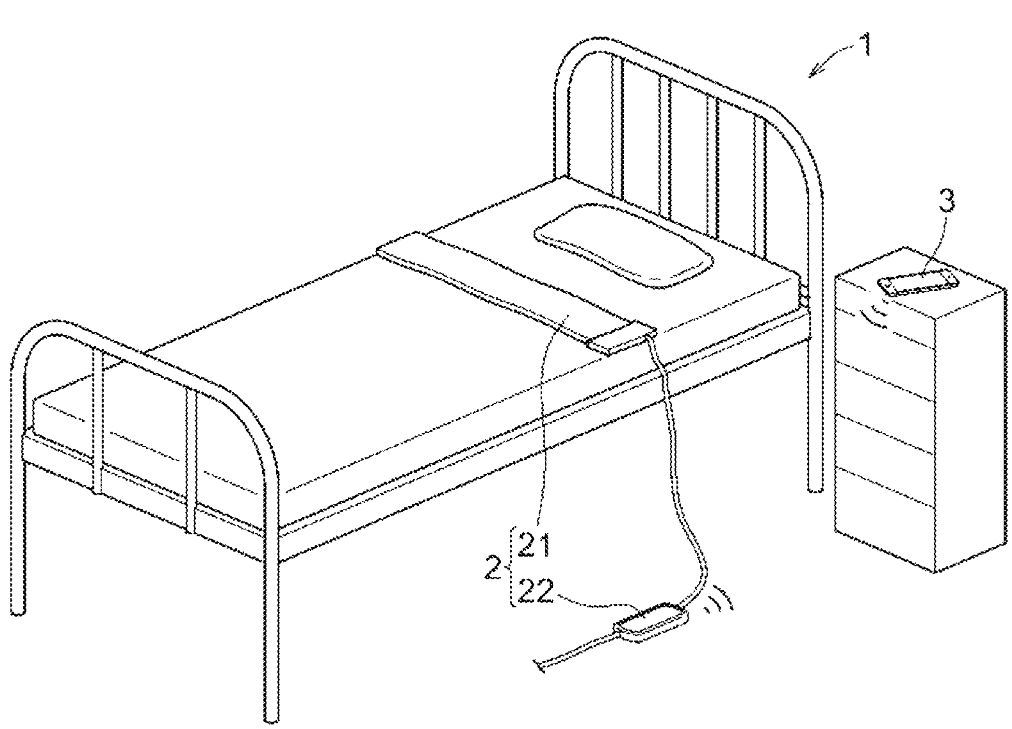
FIG. 2 schematically shows an example of installation of a measuring device.

FIG. 2 schematically shows an example of installation of the measuring device 2. The measuring device 2 is provided in a place where the subject lives (e.g., subject's home or elderly care facility), and comprises a sheet sensor 21 and a measurement unit 22.

As shown in FIG. 2, the sheet sensor 21 comprises a piezoelectric element, and is provided on the bed the subject uses on a daily basis. In FIG. 2, the bed sheet and comforter laid on the sheet sensor 21 are not shown. While the subject is lying, the sheet sensor 21 outputs a piezoelectric signal depending on the vibration applied from the subject's body.

In the present embodiment, "lying" means that the subject is lying regardless of whether the subject is asleep or not. Therefore, the sheet sensor 21 may be provided not only in a sleeping area such as bed, but also an area where the patient can lie down and rest (sofa etc.).

The measurement unit 22 is connected to the sheet sensor 21, and AD-converts the piezoelectric signal generated by the sheet sensor 21. Further, the measurement unit 22 has the function of communicating with a smartphone 4 using Bluetooth (registered trademark), and the AD-converted piezoelectric signal is temporarily saved in the smartphone 4, and then transmitted to the management device 3.

The management device 3 corresponds to the heart sound analysis device recited in the claims, and is provided at a medical institution or in the cloud. The management device 3 can be composed of a general-purpose computer, and comprises, as hardware structures, a processor such as a CPU or GPU, a main storage device such as DRAM or SRAM (not shown), and an auxiliary storage device 30 such as an HDD or SSD. The auxiliary storage device 30 stores various programs for operating the management device 3, such as a heart sound extraction program D1 and a heart sound analysis program D2. The heart sound extraction program D1 and the heart sound analysis program D2 may be downloaded to the management device 3 via a communication network, such as the Internet, or the heart sound extraction program D1 and the heart sound analysis program D2 may be recorded on a computer-readable non-transitory recording medium, such as an SD card, and then installed into the management device 3 via the storage medium.

The management device 3 comprises an acquisition unit 31, a heart sound extraction unit 32, a heart sound analysis unit 33, and a display unit 34 as functional blocks. The acquisition unit 31, the heart sound extraction unit 32, and the heart sound analysis unit 33 each may be realized in hardware using a logic circuit etc., or may be realized in software using a CPU etc. When the acquisition unit 31 and the heart sound extraction unit 32 are realized in software, it can be realized in such a manner that the CPU of the management device 3 reads the heart sound extraction program D1 to the main storage device and executes it. When the heart sound analysis unit 33 is realized in software, it can be realized in such a manner that the CPU of the management device 3 reads the heart sound analysis program D2 to the main storage device and executes it.

The management device 3 may be composed of multiple devices. For example, the parts that function as the acquisition unit 31 and the heart sound extraction unit 32 may be configured as a heart sound extraction device, and the parts that function as the heart sound analysis unit 33 and the display unit 34 may be configured as a heart sound analysis device.

The acquisition unit 31 is a functional block that acquires the piezoelectric signal from the sheet sensor 21. The acquisition unit 31 does not always need to obtain the piezoelectric signal, and may obtain the piezoelectric signal at least while the subject is lying. If the sampling frequency of the piezoelectric signal is high, the acquisition unit 31 may perform downsampling to reduce the amount of data.

Figure 3:
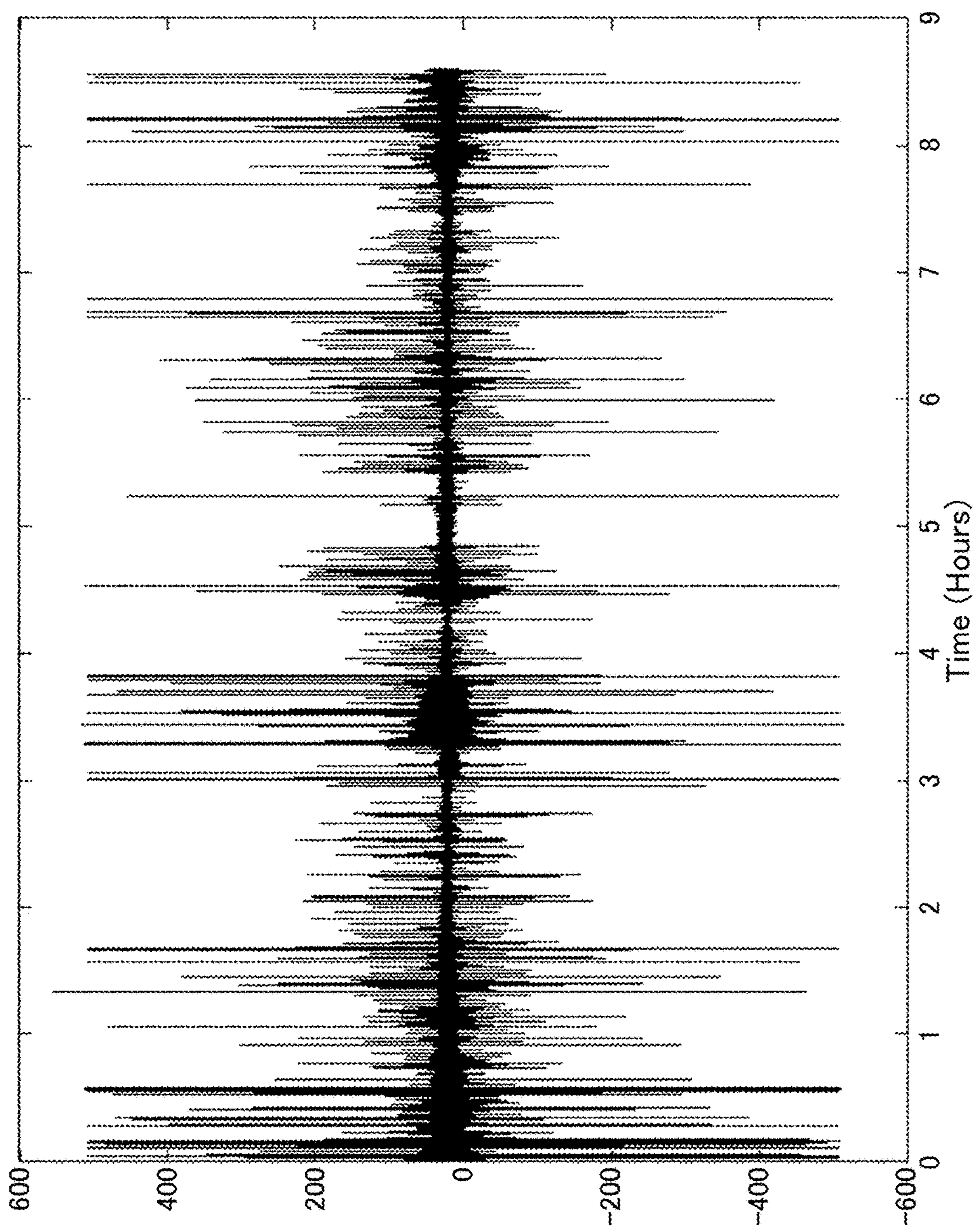
FIG. 3 shows an example of a piezoelectric signal acquired in the subject's lying period.

FIG. 3 is an example of the piezoelectric signal acquired in the subject's lying period and downsampled to 400 Hz. In most of the lying period, the piezoelectric signal includes body motion, breathing, heartbeat, and many other noise components.

Overview of Heart Sound Extraction Method

The heart sound extraction unit 32 shown in FIG. 1 is a functional block that extracts the heart sound signal of the subject from the piezoelectric signal. The heart sound signal in the piezoelectric signal is much weaker than the signals of body motion, breathing, and heart rate, and is therefore easily affected by noise etc. It was thus difficult with conventional technology to extract heart sound signals (waveforms) that could be used to correctly determine the presence or absence of extra heart sounds. Accordingly, the heart sound extraction unit 32 automatically sets a time window that can withstand high-precision heart sound analysis for the heart sound signal extracted from the piezoelectric signal.

In the present embodiment, the time window is at least one of the following time windows:

(1) a time window in which the reciprocal of the standard deviation of respiratory frequency (RST) is maximum
(2) a time window in which the periodic respiratory power (CSR) is maximum
(3) a time window in which the amplitude of the extracted heart sound signal is maximum
(4) a time window in which the amplitude variation of the extracted heart sound signal is minimum
(5) a time window of apnea in time window (2) above
(6) a time window in which the standard deviation (SD) of the heartbeat amplitude is minimum
(7) a time window in which the SD of heartbeat intervals (RR intervals) is minimum The present inventor focused on the fact that there are relatively few components other than the heart sound signals within these time frames, and found that the use of the heart sound signals within these time windows allows for high-precision heart sound analysis.

The reason for selecting time window (1) is that breathing is periodic when RST is large, making it easier to remove the influence of the respiratory signal. The reason for selecting time window (2) is that since the respiratory arrest time is long when CSR is large, it is less affected by breathing. The reason for selecting time window (3) is that a strong heart sound signal is present in this time window. The reason for selecting time window (4) is that a stable heart sound signal is present in this time window. The reason for selecting time window (5) is that during apnea, the influence of breathing can be completely removed. The reason for selecting time window (6) is that when the amplitude of the heartbeat is large, the volume (amplitude) of the heart sound may also fluctuate. The reason for selecting time window (7) is to remove the influence of variations in heart sound intervals due to variations in RR intervals. The following explains a specific example of setting a time window for extra heart sound determination.

Figure 4:
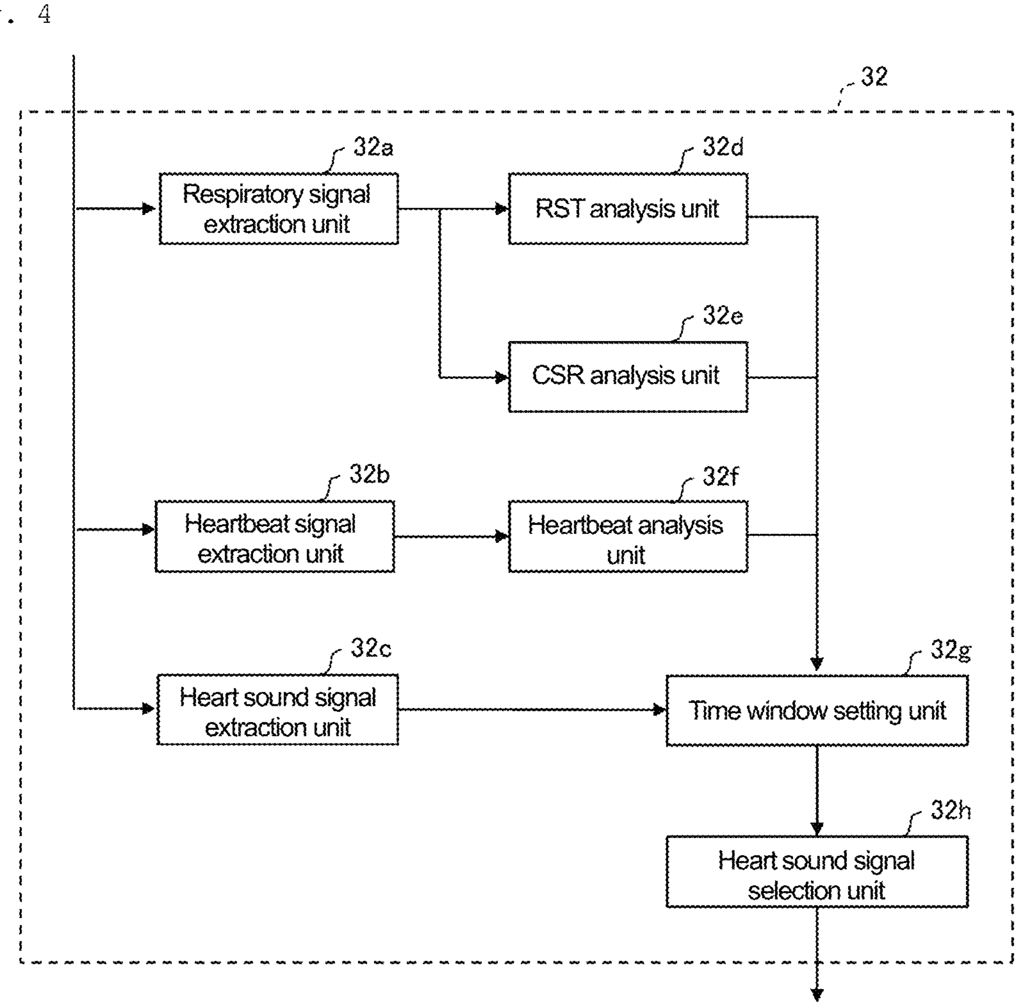
FIG. 4 is a detailed functional block diagram of a heart sound extraction unit.

FIG. 4 is a detailed functional block diagram of the heart sound extraction unit 32. The heart sound extraction unit 32 comprises a respiratory signal extraction unit 32*a*, a heartbeat signal extraction unit 32*b*, a heart sound signal extraction unit 32*c*, an RST analysis unit 32*d*, a CSR analysis unit

32*e*, a heartbeat analysis unit 32*f*, a time window setting unit 32*g*, and a heart sound signal selection unit 32*h*. The piezoelectric signal output from the acquisition unit 31 is input to the respiratory signal extraction unit 32*a*, heartbeat signal extraction unit 32*b*, and heart sound signal extraction unit 32*c*.

The respiratory signal extraction unit 32*a* extracts the respiratory signal from the piezoelectric signal. Since the respiratory signal has a relatively high signal level, it is easier to extract it while removing noise than the heart sound signal, and analysis throughout the recording time is possible. In the present embodiment, the respiratory signal extraction unit 32*a* removes noise from the piezoelectric signal at 4000 Hz, then finally downsamples the signal to 4 Hz, and extracts the respiratory signal through a band-pass filter of 0.008 to 0.6 Hz. This is output to the RST analysis unit 32*d* and CSR analysis unit 32*e*.

The RST analysis unit 32*d* calculates RST from the respiratory signal. In the present embodiment, the RST analysis unit 32*d* moves a 5-minute time window of the respiratory signal by 50 seconds to extract a signal within the window, and performs frequency analysis on the signal of each time window using the maximum entropy method. The CSR analysis unit 32*e* extracts the envelope waveform (CSR waveform) of the respiratory signal, and performs frequency analysis on the envelope waveform for each time window using the maximum entropy method. RST and CSR grades are calculated from the results of the two frequency analyses.

Figure 5:
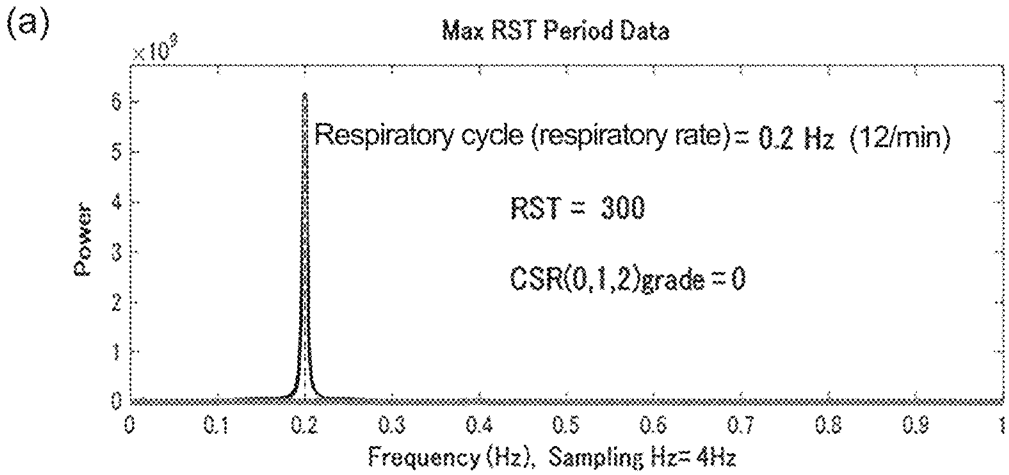
FIG. 5, panel (a) shows spectral distribution by frequency analysis in a time window with maximum RST, and FIG. 5, panel (b) shows the waveforms of the respiratory signal, CSR signal, and noise component in this time window.
Figure 5:
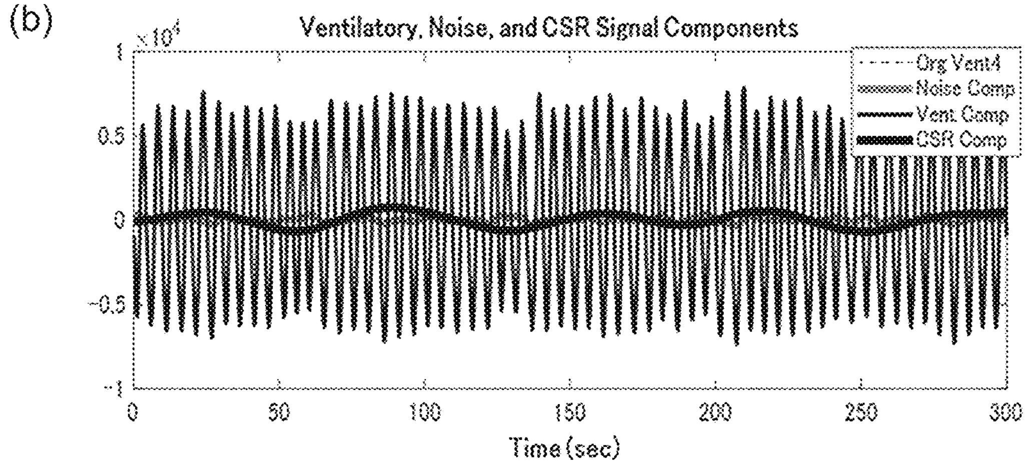

FIG. 5 (*a*) shows spectrum distribution obtained by frequency analysis in a time window with maximum RST, and FIG. 5 (*b*) shows the waveforms of the respiratory signal (black line), CSR signal (red line), and noise component (blue line) in this time window. It can be seen that when RST is maximum, breathing is highly periodic.

Figure 6:
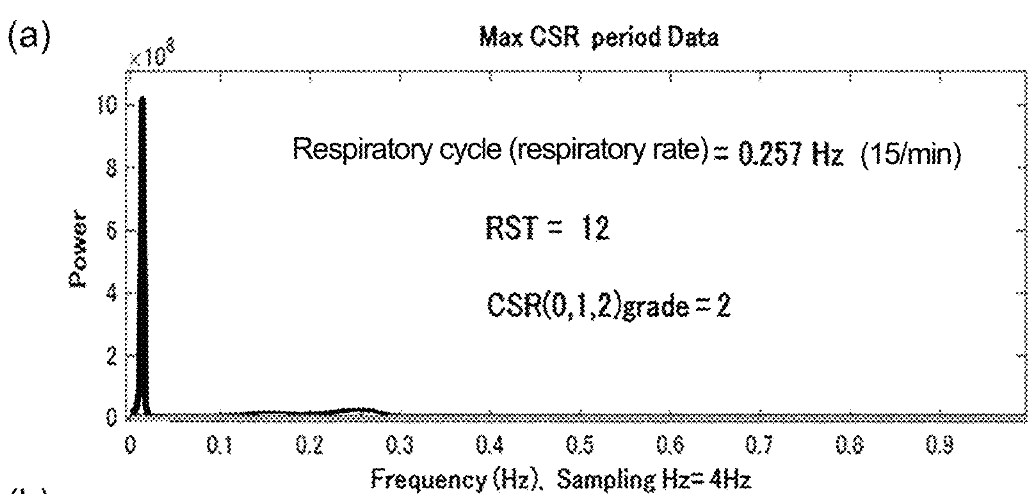
FIG. 6, panel (a) shows spectral distribution by frequency analysis in a time window with maximum CSR, and FIG. 6, panel (b) shows the waveforms of the respiratory signal, CSR signal, and noise component in this time window.
Figure 6:
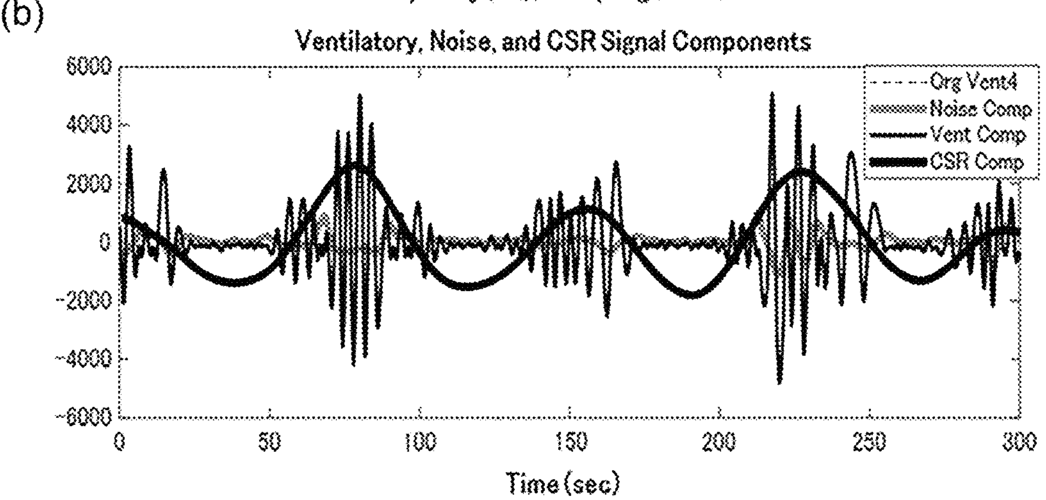

FIG. 6 (*a*) shows spectrum distribution obtained by frequency analysis in a time window with maximum CSR, and FIG. 6 (*b*) shows the waveforms of the respiratory signal (black line), CSR signal (red line), and noise component (blue line) in this time window. From these waveforms, it can be seen that while the CSR signal is significantly below zero, breathing stops, and the noise component is extremely small.

The heartbeat signal extraction unit 32*b* extracts a pulsation signal (heartbeat signal) from the piezoelectric signal. In the present embodiment, the heartbeat signal extraction unit 32*b* removes noise from the piezoelectric signal at 4000 Hz, then finally downsamples the signal to 30 Hz, and extracts the heartbeat signal through a band-pass filter of 0.8 to 2 Hz.

The heartbeat analysis unit 32*f* moves a 5-minute time window by 50 seconds for the heartbeat signal all night to extract a signal in the window, and calculates the SD of the heartbeat amplitude and the SD of RR intervals in each time window.

RST of each time window calculated by the RST analysis unit 32*d*, CSR of each time window calculated by the CSR analysis unit 32*e*, and the SD of the heartbeat amplitude and the SD of RR intervals in each time window calculated by the heartbeat analysis unit 32*f* are output to the time window setting unit 32*g*.

The heart sound signal extraction unit 32*c* extracts a heart sound signal from the piezoelectric signal. In the present embodiment, the heart sound signal extraction unit 32*c* downsamples the piezoelectric signal from 4000 Hz to 400 Hz, removes noise, and extracts the heart sound signal through a band-pass filter of 25 to 100 Hz.

Setting of Time Window Suitable for Heart Sound Analysis

The time window setting unit 32*g* sets a time window suitable for heart sound analysis in the heart sound signal based on information from the RST analysis unit 32*d*, CSR analysis unit 32*e*, heartbeat analysis unit 32*f*, and heart sound signal extraction unit 32*c*. Specifically, the time window setting unit 32*g* sets a signal of at least one of the following time windows:

(1) a time window in which RST is maximum
(2) a time window in which CSR is maximum
(3) a time window in which the amplitude of the extracted heart sound signal is maximum
(4) a time window in which the amplitude variation of the extracted heart sound signal is minimum
(5) a time window of apnea in time window (2) above
(6) a time window in which the SD of the heartbeat amplitude is minimum
(7) a time window in which the SD of RR intervals is minimum The number of time windows set by the time window setting unit 32*g* may be single or multiple; however, among these time windows, time windows (1), (2), and (5) are preferred. Further, time windows (2) and (5) are particularly preferred because they are not affected by respiratory signals.

Time window (1) is not limited to the time window with maximum RST, but may include a time window with RST equal to or greater than a predetermined value. Time window (2) is also not limited to the time window with maximum CSR, but may include a time window with CSR equal to or greater than a predetermined value. Time window (3) is also not limited to the time window in which the amplitude of the heart sound signal is maximum, but may include a time window in which the amplitude of the heart sound signal is equal to or greater than a predetermined value. Time window (4) is not limited to the time window in which the amplitude variation of the heart sound signal is minimum, but may include a time window in which the amplitude variation of the heart sound signal is equal to or less than a predetermined value. Time window (6) is also not limited to the time window in which the SD of the heartbeat amplitude is minimum, but may include a time window with in which the SD of the heartbeat amplitude is equal to or less than a predetermined value. Time window (7) is also not limited to the time window in which the SD of RR intervals is minimum, but may include a time window in which the SD of RR intervals is equal to or less than a predetermined value.

The length of each time window is 5 minutes in the present embodiment as described above, but may be appropriately changed.

The heart sound signal selection unit 32*h* selects a heart sound signal within the set time window from the heart sound signal extracted by the heart sound signal extraction unit 32*c*. In the present embodiment, the heart sound signal selection unit 32*h* cuts the heart sound signal within the time window from the heart sound signal, outputs it to the heart sound analysis unit 33, and displays the waveform of the heart sound signal within the time window on the display unit 34. The medical staff observe the waveform of the heart sound signal (more desirably together with the waveform of the heartbeat signal), thereby determining the presence or absence of extra heart sounds.

The heart sound signal selection unit 32*h* may display a frame showing a time window on the waveform of the heart sound signal without cutting out the heart sound signal within the time window, or may display the waveform within the time window in a manner distinguishable from other waveforms. As a result, the medical staff can identify the portion of the heart sound signal suitable for determining the presence or absence of extra heart sounds. Alternatively, the heart sound signal selection unit 32*h* may be configured only to cut out the heart sound signal within the time window and to output it to the heart sound analysis unit 33, and not to display the waveform.

Analysis of Heart Sound

The heart sound analysis unit 33 shown in FIG. 1 is a functional block that analyzes the heart sound signal to thereby support the prediction of the subject's state. As explained in the Background Art section, if extra heart sounds are confirmed in the heart sound signal, there may be some kind of disease in the heart. Therefore, the heart sound analysis unit 33 particularly analyzes the presence or absence of extra heart sounds to support the prediction of the subject's state.

Figure 7:
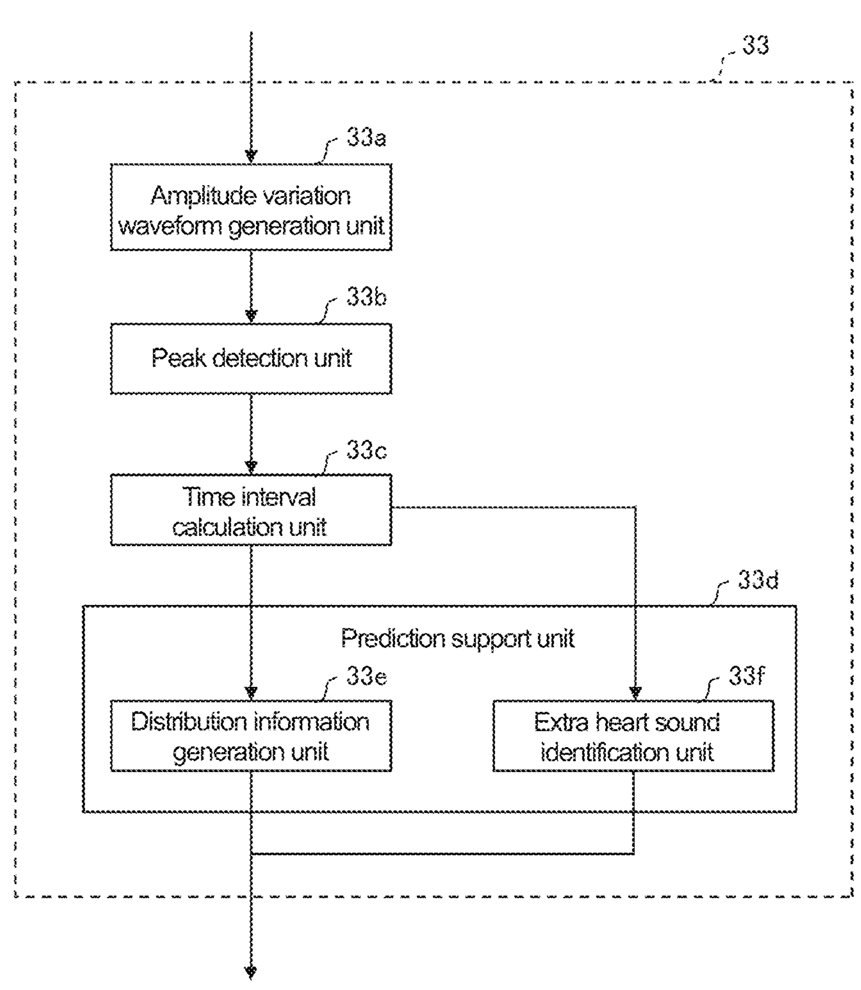
FIG. 7 is a detailed functional block diagram of a heart sound analysis unit.

FIG. 7 is a detailed functional block diagram of the heart sound analysis unit 33. The heart sound analysis unit 33 comprises an amplitude variation waveform generation unit 33*a*, a peak detection unit 33*b*, a time interval calculation unit 33*c*, and a prediction support unit 33*d*.

The amplitude variation waveform generation unit 33*a* is a functional block that generates the amplitude variation waveform of the heart sound signal. This function is explained based on FIGS. 8 and 9.

Determination of Presence or Absence of Extra Heart Sounds

Figure 8:
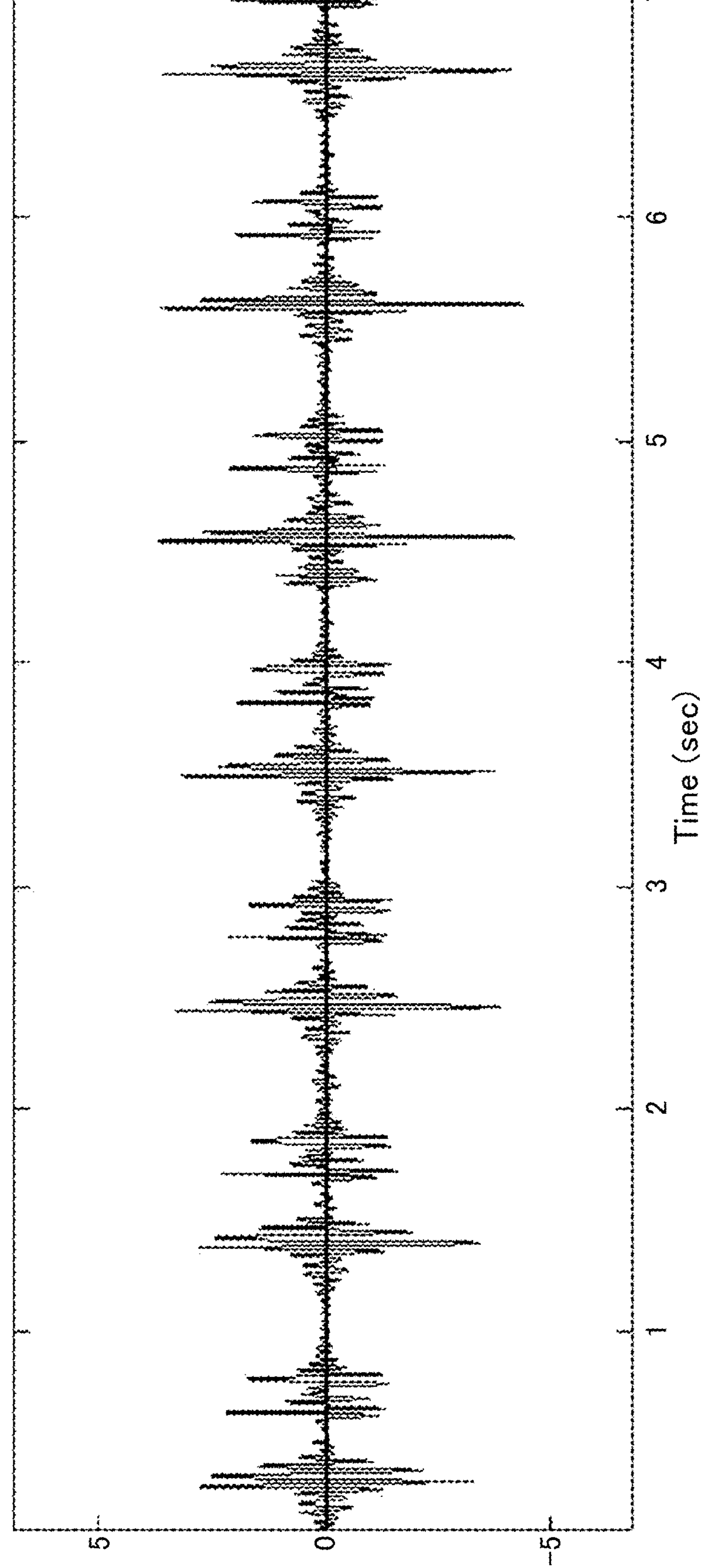
FIG. 8 shows an example of the waveform of heart sound signal extracted by the heart sound extraction unit.

FIG. 8 is an example of the waveform of the heart sound signal extracted by the heart sound extraction unit 32. In FIG. 8, waveforms with large and small amplitudes appear to repeat regularly; however, actually, the amplitude size may be random due to the influence of denoising process etc.

Figure 9:
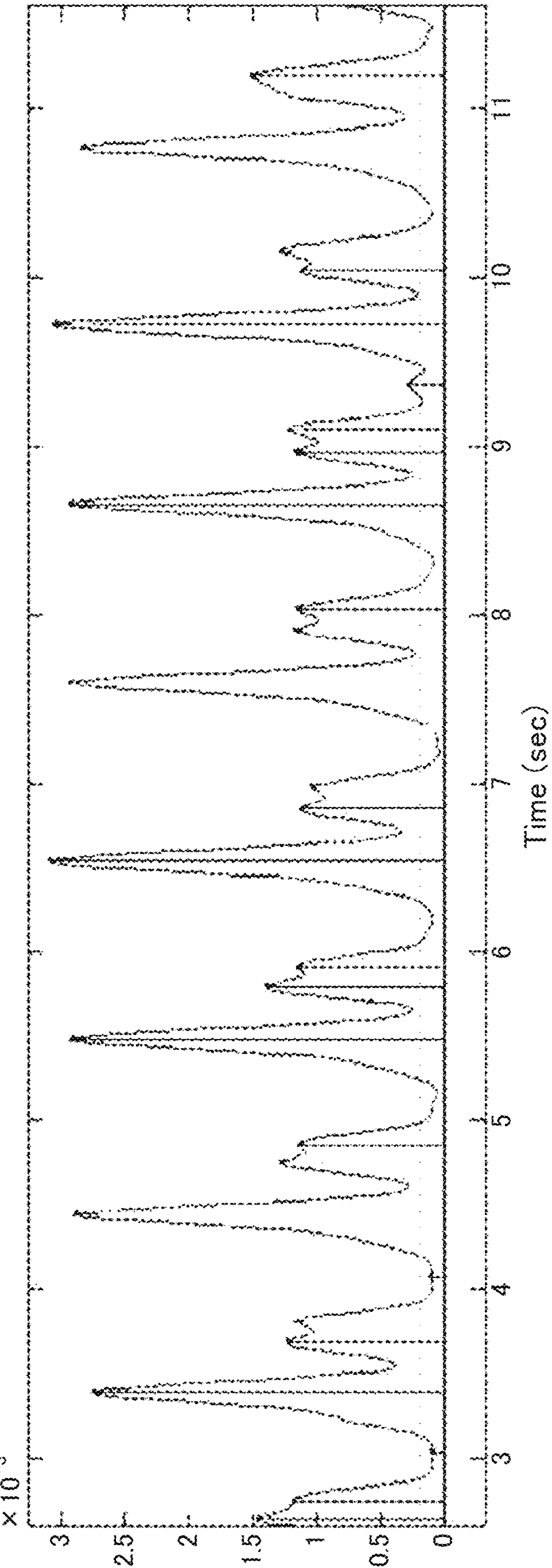
FIG. 9 shows an example of the amplitude variation waveform of the heart sound signal.

The amplitude variation waveform generation unit 33*a* sets an envelope tangent to each wave of the heart sound signal in each of the positive and negative regions for the heart sound signal of FIG. 8, and corrects the negative envelope of the two envelopes to 0, thereby generating the amplitude variation waveform shown in FIG. 9.

The peak detection unit 33*b* shown in FIG. 7 is a functional block that detects peaks in the amplitude variation waveform. In the present embodiment, peaks refer to maximum points in the amplitude variation waveform. FIG. 9 shows peaks with dots.

The time interval calculation unit 33*c* shown in FIG. 7 is a functional block that calculates the time interval of each peak. In FIG. 9, the interval of perpendicular lines extending from points indicating the peaks to the time axis corresponds to the time interval of each peak. In the following explanation, the time interval may be simply referred to as the "interval."

The prediction support unit 33*d* shown in FIG. 7 is a functional block that supports the prediction of the subject's state based on the time intervals. In the present embodiment, the prediction support unit 33*d* supports the prediction of the subject's state by generating information suggesting the presence or absence of extra heart sounds in the heart sound signal, and/or automatically determining the presence or absence of extra heart sounds. In order to realize this function, the prediction support unit 33*d* comprises a distribution information generation unit 33*e* and an extra heart sound identification unit 33*f*.

As the information suggesting the presence or absence of extra heart sounds, the distribution information generation unit 33*e* generates distribution information indicating the distribution of the time intervals calculated by the time interval calculation unit 33*c*. The generated distribution information is displayed on the display unit 34.

FIG. 10 shows an example of the distribution information. In this figure, time intervals between each peak and its immediately preceding peak are indicated with circles. From this figure, it can be intuitively understood that the time intervals include three groups: a group of about 0.1 seconds, a group of about 0.3 to 0.5 seconds, and a group of about 0.6 seconds.

Figure 11:
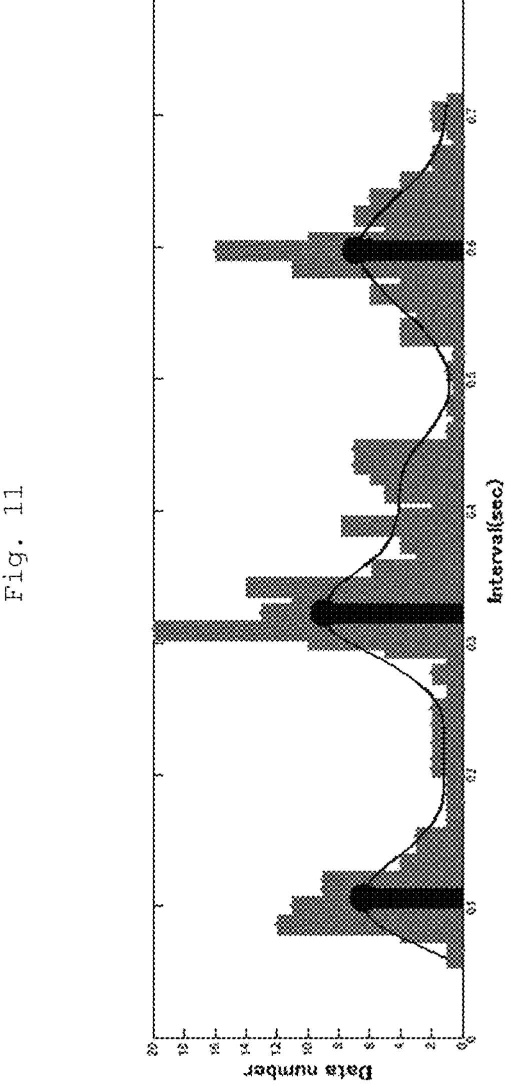
FIG. 11 shows an example of distribution information in a histogram format.

The distribution information generation unit 33*e* can also generate the distribution information in a histogram format. FIG. 11 shows an example of the distribution information in a histogram format. In this figure, the horizontal axis represents the time interval with the immediately preceding peak, and the vertical axis represents the number of peaks that have this time interval. From this histogram, it can be intuitively understood that the peak time intervals can be divided into 3 groups.

The number of time interval groups serves as an indicator to predict the presence or absence of extra heart sounds. In general, the heart sound of a healthy adult includes only sounds I and II in one heartbeat period (RR interval). In that case, there is the following tendency: interval between sound II and sound I in the next heartbeat period<interval between sound I and sound II. Therefore, the number of peak time interval groups is 2.

On the other hand, when sound III is present, there is the following tendency: interval between sound II and sound III<interval between sound I and sound II<interval between sound III and sound I in the next heartbeat period. Further, when sound IV is present in place of sound III (sounds III and IV are rarely present at the same), there is the following tendency: interval between sound IV and sound I in the next heartbeat period<interval between sound I and sound II<interval between sound II and sound IV. Therefore, when sound III or IV is present, the number of peak time interval groups is 3.

Thus, from the distribution information generated by the distribution information generation unit 33*e*, if the number of peak time interval groups can be understood, it is possible to predict the presence or absence of extra heart sounds in the heart sound without referring to the heartbeat signal. That is, in the heart sound signal shown in FIG. 8, the number of peak time interval groups in the amplitude variation waveform is 3, whereby it can be predicted that extra heart sounds are present.

When peaks are accurately detected by the peak detection unit 33*b*, the average time interval is calculated for each of the above groups, and the average total value is approximately equal to the average heart sound cycle. Accordingly, when the heartbeat is measured, the accuracy of the detection of peaks by the peak detection unit 33*b* can be determined by comparing the above total value with the average RR interval of the heartbeat. That is, the closer the above total value is to the average RR interval, the more accurately peaks are detected based on the waveform of the heart sound, which indicates a high reliability of the prediction of extra heart sounds.

Therefore, when multiple time windows are selected, it is preferable to use a prediction result with high reliability among prediction results obtained from heart sound signals extracted from the respective time windows.

Determination of Type of Extra Heart Sound

Since the interval between sound II and sound III is almost equal to the interval between sound IV and sound I in the next heartbeat period, the presence or absence of extra heart sounds can be predicted from the distribution information; however, it is difficult to determine whether the type of extra heart sound is sound III or sound IV. In contrast, the extra heart sound identification unit 33*f* shown in FIG. 7 has the function of automatically determining not only the presence or absence of extra heart sounds in the heartbeat signal, but also the type of extra heart sound, based on the peak time intervals. The determination method by the extra heart sound identification unit 33*f* is explained below with reference to FIGS. 12 to 14.

Figure 12:
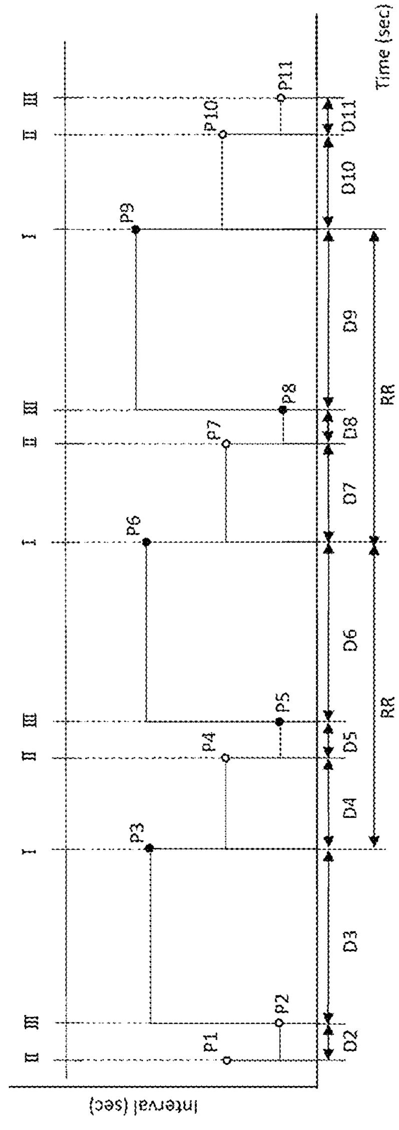
FIG. 12 is a graph plotting peaks of the amplitude variation waveform of the heart sound signal including sound III, with the time on the x-axis and the time interval with the immediately preceding peak on the y-axis.

FIG. 12 is a graph plotting peaks of the amplitude variation waveform of the heart sound signal including sound III, with the time on the x-axis and the time interval with the immediately preceding peak on the y-axis. This graph shows 11 peaks P1 to P11. The height of each peak is equal to the time interval with the immediately preceding peak. When the time interval between (n−1)th peak Pn−1 and nth peak Pn is taken as Dn, the height of peak Pn is Dn. That is, all the quadrilaterals in the graph are squares. Each peak is associated with symbol I, II, or III to indicate the type of heart sound; however, these are shown for convenience only. The extra heart sound identification unit 33*f* does not determine into which heart sound each peak is classified.

The extra heart sound identification unit 33*f* searches for maximum and minimum peaks from the peaks. The maximum peak refers to a peak higher than the preceding and following peaks, and the minimum peak refers to a peak lower than the preceding and following peaks. That is, the maximum peak satisfies the following condition:

$$Dn-1<Dn>Dn+1, \quad \text{A}$$

and the minimum peak satisfies the following condition:

$$Dn-1>Dn<Dn+1. \quad \text{B}$$

For example, peak P3 is a maximum peak because it satisfies D2<D3>D4 and satisfies condition A. Peaks P6 and P9 are also maximum peaks because they satisfy condition A.

Peak P5 is a minimum peak because it satisfies D4>D5<D6 and satisfies condition B. Peak P8 is also a minimum peak because it satisfies condition A.

On the other hand, peak P4 does not correspond to either a maximum peak or a minimum peak because it satisfies D3>D4>D5 and does not satisfy condition A or B. Similarly, peaks P7 and P10 do not correspond to either a maximum peak or a minimum peak.

In FIG. 12, the maximum and minimum peaks are indicated with black circles, and peaks that do not correspond to either a maximum peak of a minimum peak are indicated with white circles. For peaks P1, P2, and P11, time intervals necessary to determine whether they are maximum or minimum peaks within the graph range are omitted; thus, they are not subjects to this determination and are indicated with white circles.

Subsequently, the extra heart sound identification unit 33*f* selects any maximum peak as a first peak from the searched maximum peaks, selects the minimum peak immediately following the first peak as a second peak, and selects the maximum peak immediately following the second peak as a third peak. In this case, the time interval between the first and third peaks can be regarded as equal to the RR interval (hereinafter, RR) of the heartbeat. In FIG. 12, the first peak, second peak, and third peak correspond to a combination of peaks P3, P5, and P6, and a combination of peaks P6, P8, and P9.

Subsequently, the extra heart sound identification unit 33*f* calculates the ratio R of the time interval between the second and third peaks to the time interval between the first and second peaks. For example, when the first peak, second peak, and third peak are peaks P3, P5, and P6, respectively, the following equation holds:

$$R=(D4+D5)/D6 \quad \text{(C)}$$

As described later, the ratio R serves as an indicator for determining the presence or absence of extra heart sounds in the heart sound signal and the type of extra heart sound.

Figure 13:
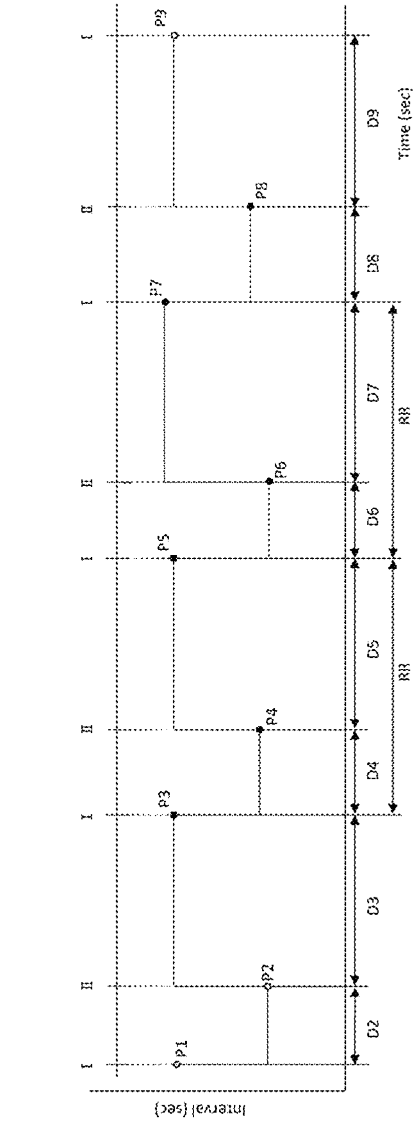
FIG. 13 is a graph plotting peaks of the amplitude variation waveform of the heart sound signal not including sounds III and IV, with the time on the x-axis and the time interval with the immediately preceding peak on the y-axis.
Figure 14:
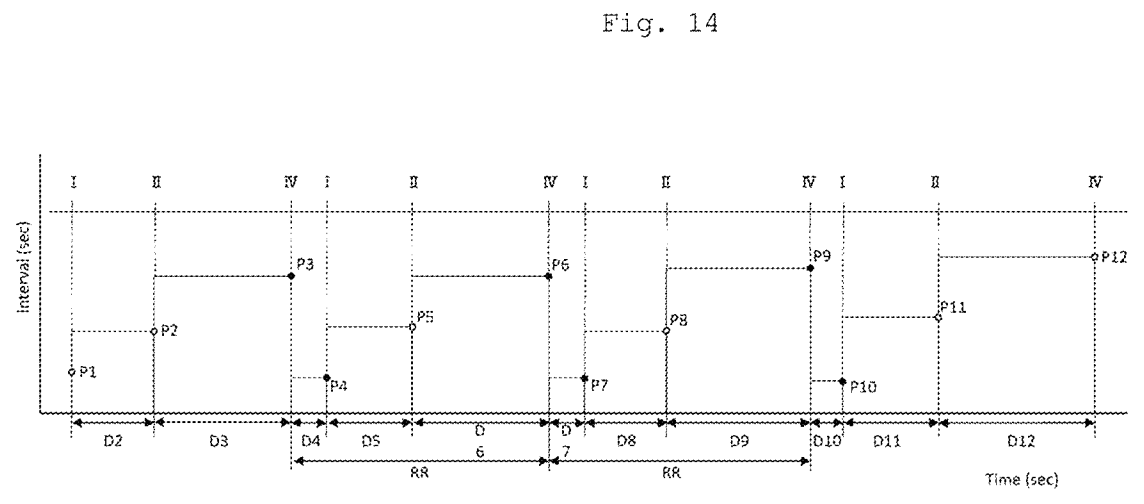

FIG. 13 is a graph plotting peaks of the amplitude variation waveform of the heart sound signal not including sounds III and IV, with the time on the x-axis and the time interval with the immediately preceding peak on the y-axis, and FIG. 14 is a graph plotting peaks of the amplitude variation waveform of the heart sound signal including sound IV, with the time on the x-axis and the time interval with the immediately preceding peak on the y-axis. The definition of each symbol in these graphs is the same as that of FIG. 12. The calculation of the ratio R from the graphs of FIGS. 13 and 14 is explained below.

The graph shown in FIG. 13 shows 9 peaks P1 to P9. Each peak is associated with symbol I or II; however, these are shown for convenience only. The extra heart sound identification unit 33*f* does not determine into which heart sound each peak is classified.

The extra heart sound identification unit 33*f* searches for maximum peaks that satisfy condition A and minimum peaks that satisfy condition B from the peaks. The maximum peaks correspond to peaks P3, P5, and P7, and the minimum peaks correspond to peaks P4, P6, and P8. Peaks P1, P2, and P9 are indicated with white circles. Since time intervals necessary to determine whether they are maximum or minimum peaks within the graph range are omitted, these white circles mean that they are not subjects to this determination. In FIG. 14, there are no peaks that do not correspond to the maximum or minimum peaks.

Subsequently, the extra heart sound identification unit 33*f* selects a first peak, a second peak, and a third peak from the searched maximum and minimum peaks, and calculates the ratio R of the time interval between the second and third peaks to the time interval between the first and second peaks. For example, when the first peak, second peak, and third peak are peaks P3, P4, and P5, respectively, the following equation holds:

$$R=D4/D5 \quad \text{(D).}$$

The graph shown in FIG. 14 shows 12 peaks P1 to P12. Each peak is associated with symbol I, II, or IV; however, these are shown for convenience only. The extra heart sound identification unit 33*f* does not determine into which heart sound each peak is classified.

The extra heart sound identification unit 33*f* searches for maximum peaks that satisfy condition A and minimum peaks that satisfy condition B from the peaks. The maximum peaks correspond to peaks P3, P6, and P9, and the minimum peaks correspond to peaks P4, P7, and P10.

Subsequently, the extra heart sound identification unit 33*f* selects a first peak, a second peak, and a third peak from the searched maximum and minimum peaks, and calculates the ratio R of the time interval between the second and third peaks to the time interval between the first and second peaks. For example, when the first peak, second peak, and third peak are peaks P3, P4, and P6, respectively, the following equation holds:

$$R=D4/(D5+D6) \quad \text{(E)}$$

If the heart sound signal includes sound III, as shown in FIG. 12, there is the following tendency: interval between sound II and sound III<interval between sound I and sound II<interval between sound III and sound I in the next heartbeat period. Therefore, the maximum peak corresponds to sound I, and the minimum peak corresponds to sound III. That is, the ratio R calculated by formula (C) means interval between sound I and sound III/interval between sound III and sound I in the next heartbeat period.

On the other hand, if the heart sound signal includes only sounds I and II, as shown in FIG. 13, there is the following tendency: interval between sound II and sound I in the next heartbeat period<interval between sound I and sound II. Therefore, the maximum peak corresponds to sound I, and the minimum peak corresponds to sound III, as in FIG. 12. That is, the ratio R calculated by formula (D) means interval between sound I and sound II/interval between sound II and sound I in the next heartbeat period. Since sound III is emitted after sound II, the ratio R calculated by formula (C) tends to be larger than the ratio R calculated by formula (D).

Further, if the heart sound signal includes sound IV, as shown in FIG. 14, there is the following tendency: interval between sound IV and sound I in the next heartbeat period<interval between sound I and sound II<interval between sound II and sound IV. Therefore, the maximum peak corresponds to sound IV, and the minimum peak corresponds to sound I. That is, the ratio R calculated by formula (E) means interval between sound IV and sound I in the next heartbeat period/interval between sound I and sound IV. Since the interval between sound IV and sound I in the next heartbeat period is very short, the ratio R calculated by formula (E) tends to be smaller than the ratios R calculated by formulas (C) and (D).

Therefore, by setting 5 thresholds for the ratio R, it is possible to determine the presence or absence of extra heart sounds in the heart sound signal, and whether the type of extra heart sound is sound III or sound IV. In the present embodiment, thresholds a, b, c, d, and e ($a<b<c<d<e$) are set, and if it is clear that there are three peak time interval groups in paragraph [0052], the extra heart sound identification unit 33*f* can determine that sound IV is likely to be present when R is smaller than threshold c, and that sound III is likely to be present when R is larger than threshold c. Further, when $a<R<b$, the probability of the presence of sound IV is increased, and when $d \leq R<e$, the probability of the presence of sound III is increased. The values of a, b, c, d, and e can be appropriately set depending on, for example, the sex and heart rate (RR interval) of the subject.

For example, for both a male and a female, a and b can be set as follows:

$$a = \frac{0.1}{(60 \div \text{heart rate} - 0.1)}$$

$$b = \frac{0.2}{(60 \div \text{heart rate} - 0.2)}$$

c is an average ratio when there is no sound III or IV, and can be set as follows for a male:

$$c = \frac{(-0.00158 \times \text{heart rate} + 0.392)}{[60 \div \text{heart rate} - (-0.00158 \times \text{heart rate} + 0.392)]}$$

For a female, c can be set as follows:

$$c = \frac{(-0.00158 \times \text{heart rate} + 0.412)}{[60 \div \text{heart rate} - (-0.00158 \times \text{heart rate} + 0.412)]}$$

Further, d and e can be set as follows for a male:

$$d = \frac{(-0.00158 \times \text{heart rate} + 0.492)}{[60 \div \text{heart rate} - (-0.00158 \times \text{heart rate} + 0.492)]}$$

$$e = \frac{(-0.00158 \times \text{heart rate} + 0.592)}{[60 \div \text{heart rate} - (-0.00158 \times \text{heart rate} + 0.592)]}$$

For a female, d and e can be set as follows:

$$d = \frac{(-0.00158 \times \text{heart rate} + 0.512)}{[60 \div \text{heart rate} - (-0.00158 \times \text{heart rate} + 0.512)]}$$

$$e = \frac{(-0.00158 \times \text{heart rate} + 0.612)}{[60 \div \text{heart rate} - (-0.00158 \times \text{heart rate} + 0.612)]}$$

The determination results are displayed on the display unit 34.

Figure 15:
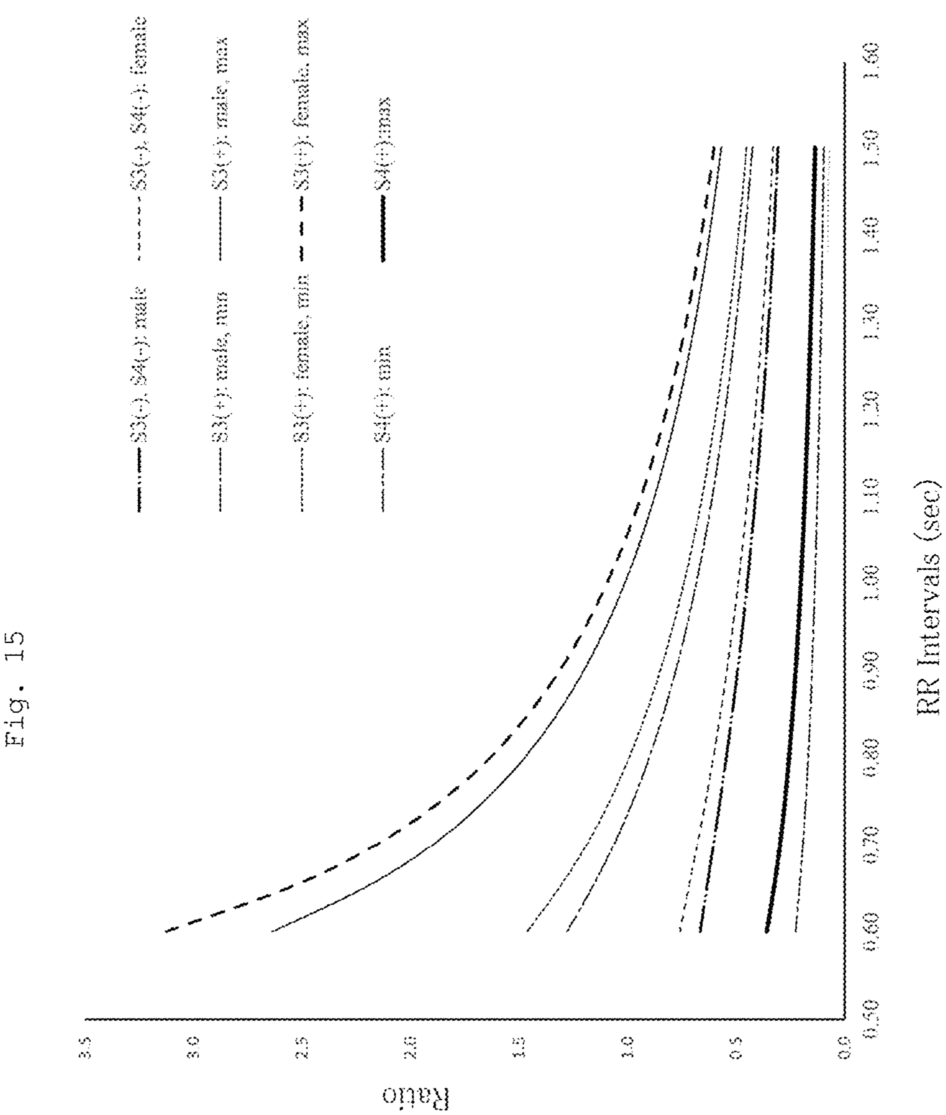
FIG. 15 shows an example of a graph for determining extra heart sounds.

FIG. 15 shows an example of a graph for determining extra heart sounds based on the ratio R. In this graph, when the ratio R according to RR intervals is plotted, if the male is located in the area above the "S3(+): male, min" curve and the female is located in the area below the "S3(+): female, min" curve, it is determined that sound III is present. Further, if both are located in the area below the "S4 (+): max" curve, it is determined that sound IV is present.

As described above, the extra heart sound identification unit 33*f* searches for maximum and minimum peaks from the amplitude variation waveform of the heart sound signal, selects first, second, and third peaks from the searched maximum and minimum peaks, calculates the ratio R of the time interval between the second and third peaks to the time interval between the first and second peaks, and determines the presence or absence of extra heart sounds in the heart sound signal and the type of extra heart sound based on the ratio R. The extra heart sound identification unit 33*f* may select multiple combinations of first, second, third peaks. In this case, the above determination may be made based on the average ratio R calculated from each combination.

BRIEF SUMMARY

In the present embodiment, a signal of a specific time window is selected from the piezoelectric signal from the sheet sensor while the subject is lying, and components other than the heart sound are removed from the selected signal. Accordingly, the heart sound signal of the subject can be extracted with high accuracy using the sheet sensor. This makes it possible to acquire the heart sound signal of a subject staying at home using the sheet sensor, and to automatically determine the presence or absence of extra heart sounds etc. by analyzing the heart sound signal. Therefore, the state of a subject under home care can be monitored remotely based on the heart sound of the subject, and the burden on the subject and medical staff can be significantly reduced.

Further, in the present embodiment, peak time intervals in the amplitude variation waveform of the heart sound signal acquired from the subject are calculated, and distribution information indicating the distribution of the time intervals is generated. This makes it possible to predict the presence or absence of extra heart sounds, which takes skill to listen to, even without referring to the heartbeat signal. Further, maximum and minimum peaks that satisfy specific conditions are searched from the peaks, and from the ratio of time intervals in the consecutive maximum peak, minimum peak, and maximum peak (first to third peaks), it is possible to determine not only the presence or absence of extra heart sounds, but also the type of extra heart sound. This can support the prediction of the subject's state.

Additional Notes

The embodiment of the present invention is described above; however, the present invention is not limited to the above embodiment, and various modifications can be made without departing from the gist thereof.

In the above embodiment, the heart sound signal of the subject is acquired by extraction from the piezoelectric signal of the sheet sensor; however, the present invention is not limited thereto. For example, the heart sound signal of the subject may be acquired by using an electronic stethoscope or a high-performance microphone, and the signal may be analyzed to determine the presence or absence of extra heart sounds.

EXAMPLES

Examples of the present invention are described below; however, the present invention is not limited to the following Examples. In each Example, the measuring device 2 of the above embodiment was used to extract the heart sound signal of the subject from the piezoelectric signal of the sheet sensor, and the heart sound signal was analyzed in the management device 3.

Example 1

In Example 1, the target was subject X, who had been diagnosed for the presence of sound III in heart sounds by routine examination. Heart sound signals were extracted from the signals of the following time windows (1) and (5) to (7) in the piezoelectric signal obtained while subject X was lying on the sheet sensor, and extra heart sounds were determined based on peak time intervals detected from the amplitude variation waveform of the heart sound signals.

(1) a time window with maximum RST (5) a time window of apnea in time window (2) above (6) a time window in which the SD of the heartbeat amplitude is minimum (7) a time window in which the SD of RR intervals is minimum.

Figure 16:
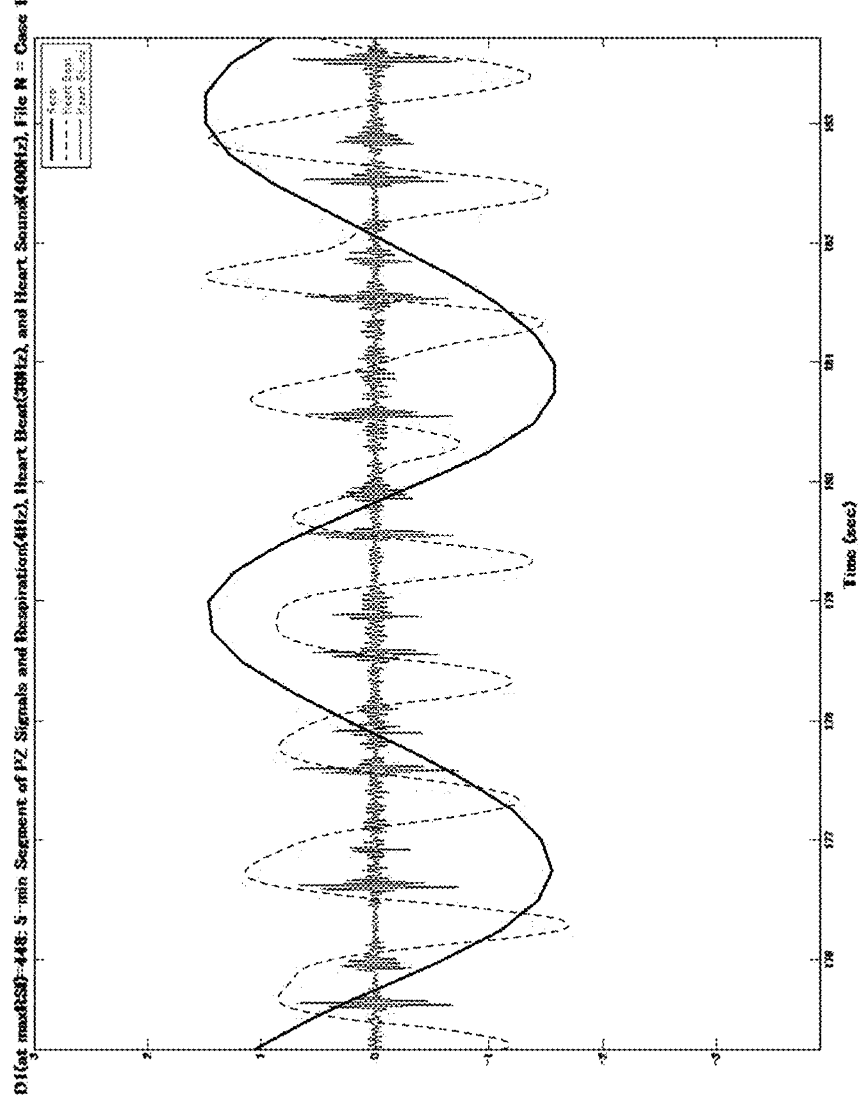
FIG. 16 shows the waveforms of heart sound signal etc. extracted from a time window with maximum RST.
Figure 17:
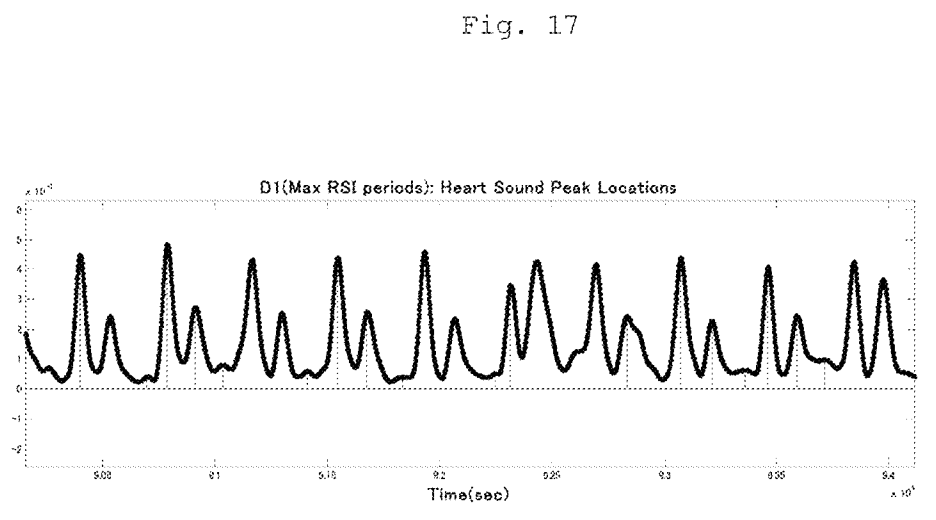
Figure 18:
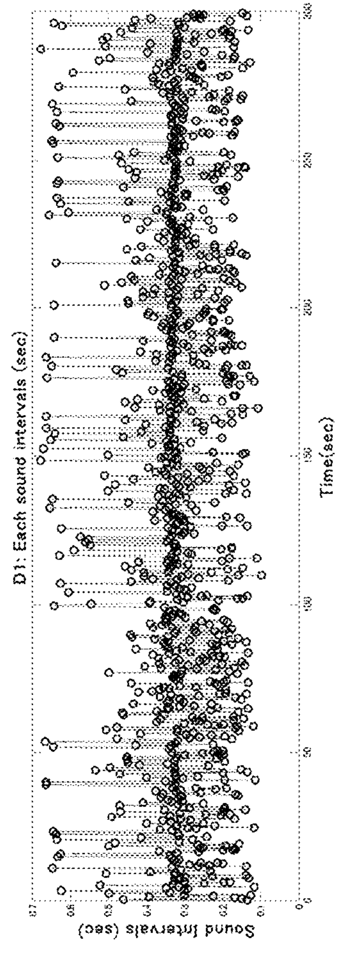
FIG. 18 shows distribution information of peak time intervals detected from the amplitude variation waveform shown in FIG. 17.

FIG. 16 shows the waveforms of the heart sound signal (black), heartbeat signal (red), and respiratory signal (blue) extracted from time window (1). FIG. 17 shows the amplitude variation waveform of the heart sound signal shown in FIG. 16. FIG. 18 shows distribution information indicating the distribution of peak time intervals detected from the amplitude variation waveform shown in FIG. 17, and FIG. 19 shows the distribution information in a histogram format.

Figure 19:
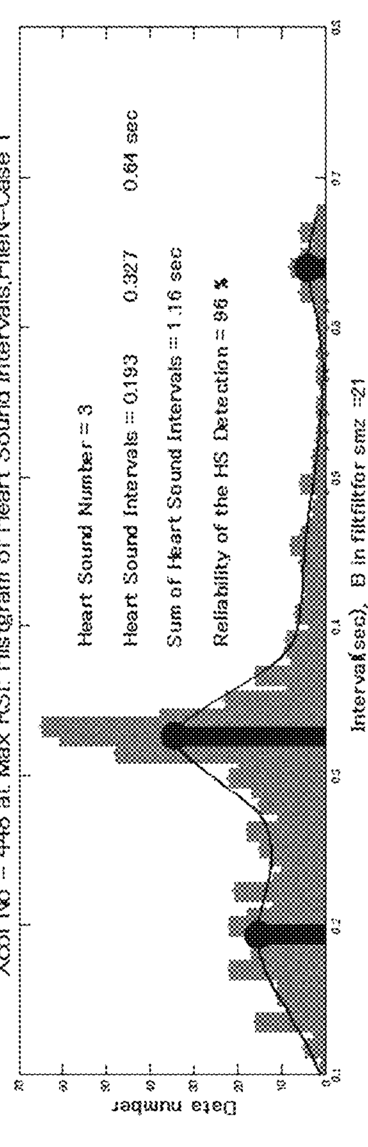
FIG. 19 shows the distribution information shown in FIG. 18 in a histogram format.

Since the peak time intervals are roughly divided into 3 groups in FIGS. 17 to 19, it can be predicted that the heart sound signals include extra heart sounds. The average time interval of each group was 0.193 sec, 0.327 sec, and 0.64 sec, and their total value (predicted heartbeat cycle) was 1.16 sec, whereas the average RR interval was 1.112 sec. Therefore, the prediction reliability was 1.112/1.16=96%.

Figure 20:
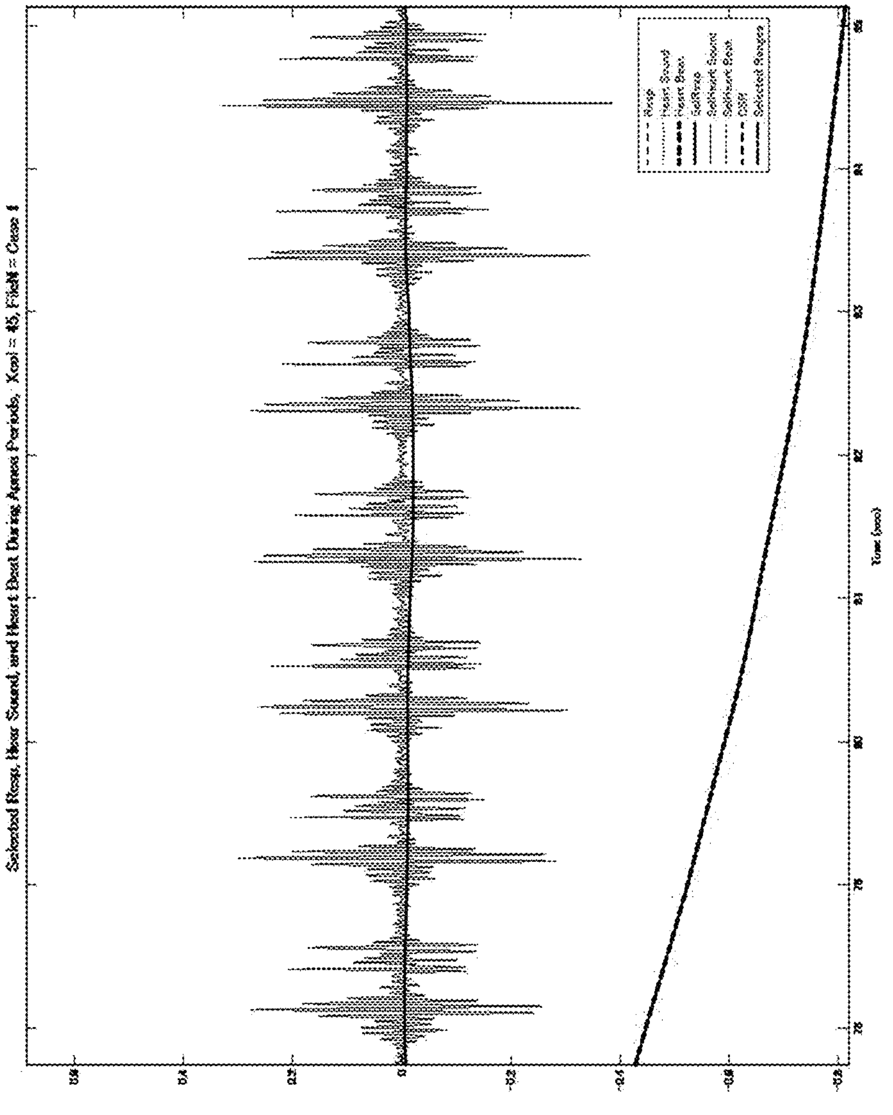
FIG. 20 shows the waveforms of heart sound signal etc. extracted from the time window of apnea in a time window with maximum CSR.
Figure 21:
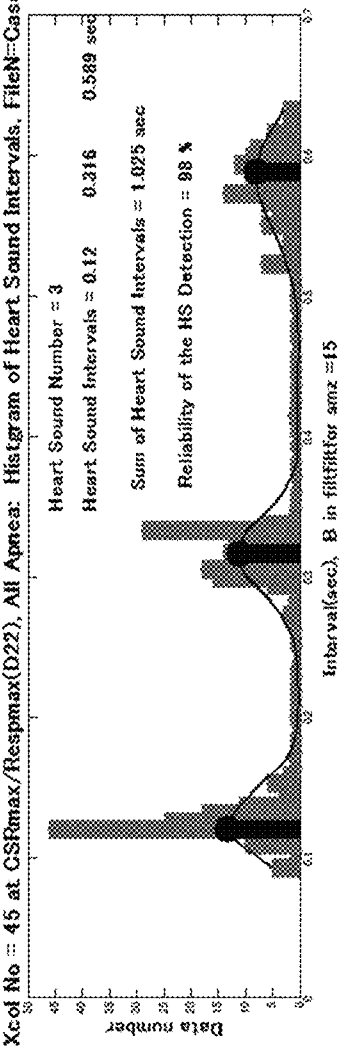
FIG. 21 shows the histogram of the distribution of peak time intervals detected from the amplitude variation waveform of the heart sound signal shown in FIG. 20.

FIG. 20 shows the waveforms of the heart sound signal (black), CSR signal (red), and respiratory signal (blue) extracted from time window (5). FIG. 21 shows the histogram of the distribution of peak time intervals detected from the amplitude variation waveform of the heart sound signal shown in FIG. 20.

Since the peak time intervals are roughly divided into 3 groups in FIG. 21, it can be predicted that the heart sound signals include extra heart sounds. The average time interval of each group was 0.12 sec, 0.316 sec, and 0.589 sec, and their total value (predicted heartbeat cycle) was 1.025 sec, whereas the average RR interval was 1.009 sec. Therefore, the prediction reliability was 1.025/1.009=98%.

Figure 22:
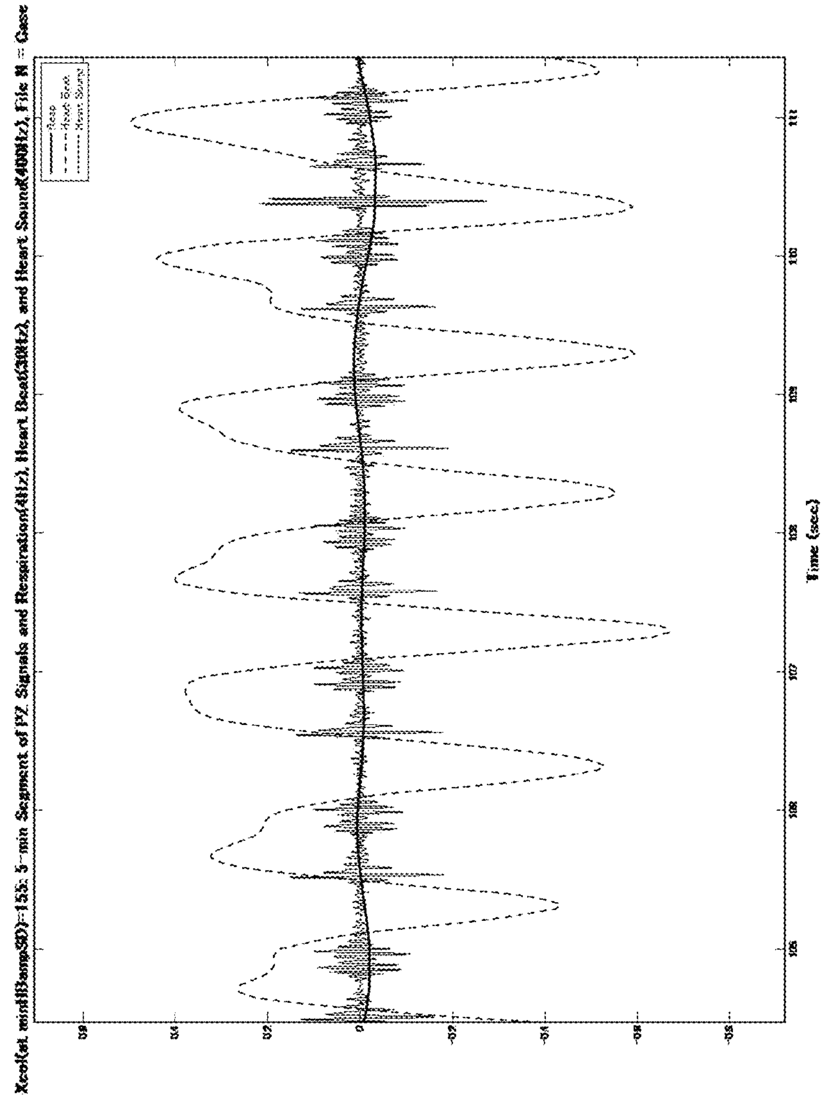
FIG. 22 shows the waveforms of heart sound signal etc. extracted from a time window in which the SD of the heartbeat amplitude is minimum.
Figure 23:
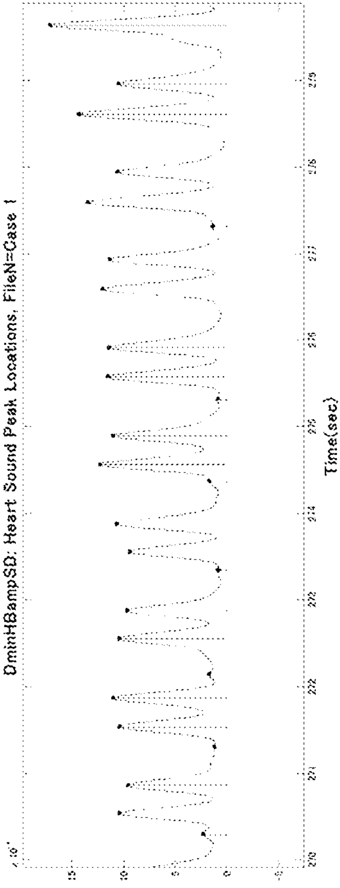
FIG. 23 shows the amplitude variation waveform of the heart sound signal shown in FIG. 22.
Figure 24:
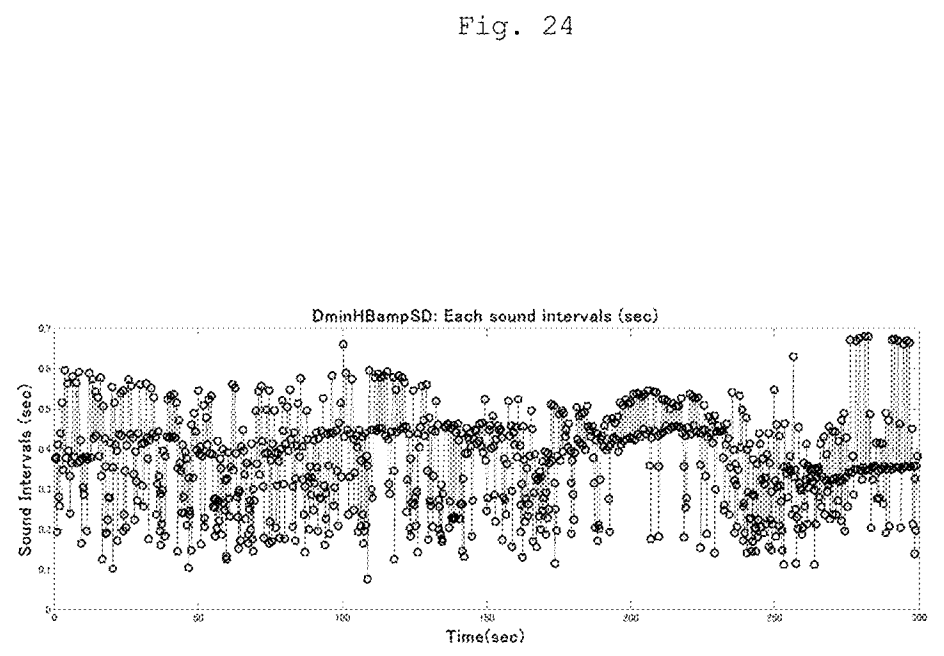

FIG. 22 shows the waveforms of the heart sound signal (black), heartbeat signal (red), and respiratory signal (blue) extracted from time window (6). FIG. 23 shows the amplitude variation waveform of the heart sound signal shown in FIG. 22. FIG. 24 shows distribution information indicating the distribution of peak time intervals detected from the amplitude variation waveform shown in FIG. 23, and FIG. 25 shows the distribution information in a histogram format.

In FIGS. 24 and 25, groups of peak time intervals are not clear; however, as a result of automatically analyzing the histogram, it was determined that they were divided into 3 groups. It can be predicted that the heart sound signals include extra heart sounds. The average time interval of each group was 0.205 sec, 0.356 sec, and 0.429 sec, and their total value (predicted heartbeat cycle) was 0.99 sec, whereas the average RR interval was 0.973 sec. Therefore, the prediction reliability was 0.973/0.99=98%.

Figure 26:
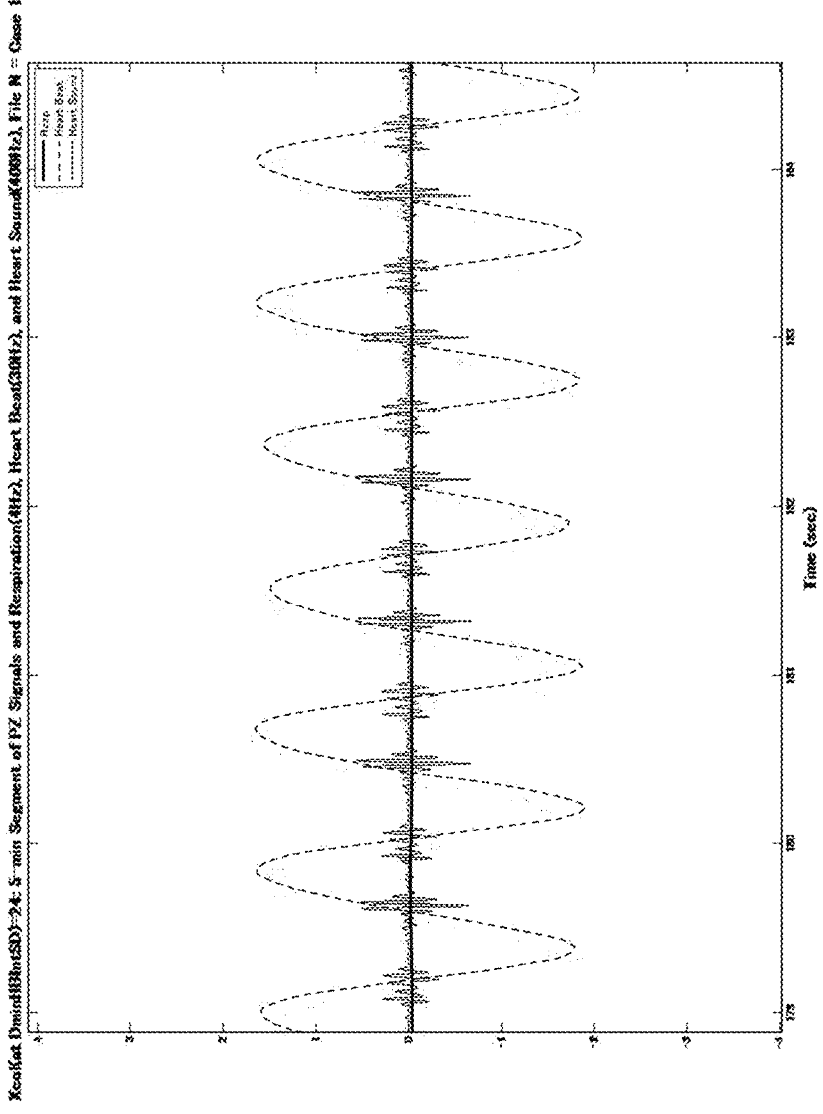
FIG. 26 shows the waveforms of heart sound signal etc. extracted from a time window in which the SD of RR intervals is minimum.
Figure 27:
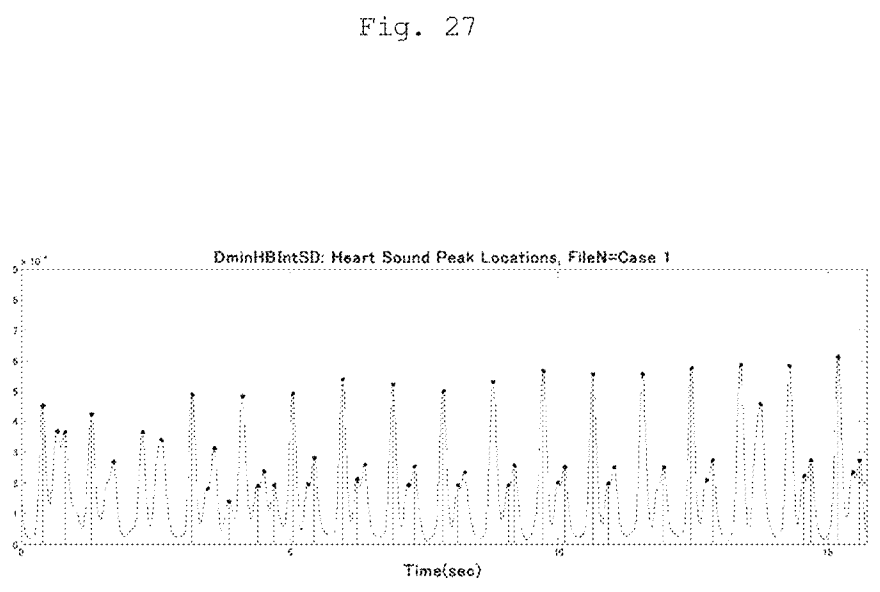
Figure 28:
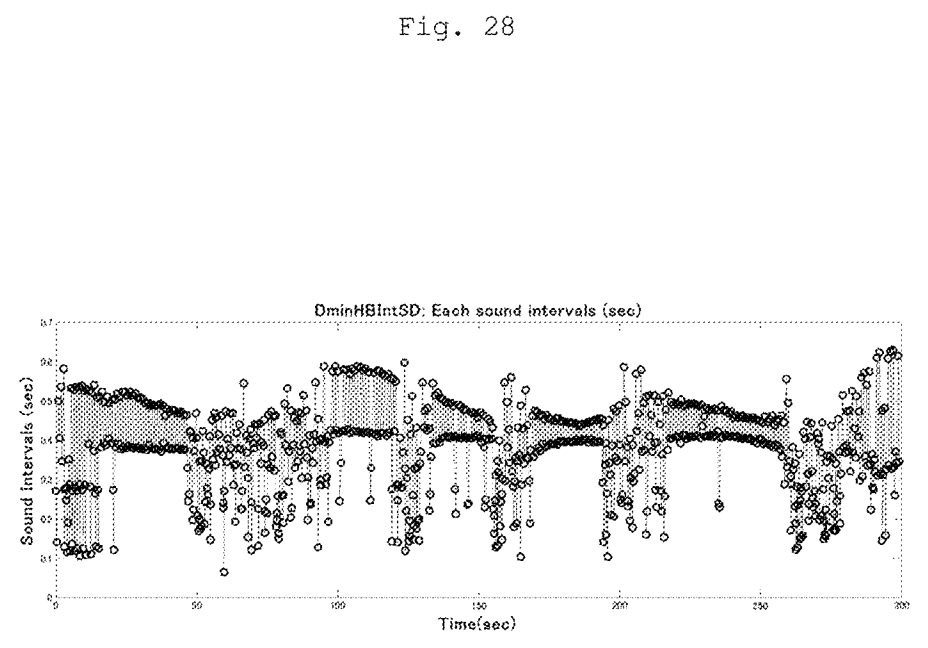

FIG. 26 shows the waveforms of the heart sound signal (black), heartbeat signal (red), and respiratory signal (blue) extracted from time window (7). FIG. 27 shows the amplitude variation waveform of the heart sound signal shown in FIG. 26. FIG. 28 shows distribution information indicating the distribution of peak time intervals detected from the amplitude variation waveform shown in FIG. 27, and FIG. 29 shows the distribution information in a histogram format.

In FIGS. 28 and 29, groups of peak time intervals are not clear; however, as a result of automatically analyzing the histogram, it was determined that they were divided into 2 groups (i.e., it was predicted that heart sound signals did not include extra heart sounds). The average time interval of each group was 0.271 sec and 0.401 sec, and their total value (predicted heartbeat cycle) was 0.672 sec, whereas the average RR interval was 0.931 sec. Therefore, the prediction reliability was 0.672/0.931=72%.

From the above, the prediction based on the heart sound signals extracted from time windows (1), (5), and (6) included extra heart sounds, whereas the prediction based on the heart sound signal extracted from time window (5) did not include extra heart sounds. However, the reliability of the prediction based on the heart sound signals extracted from time windows (1), (3), and (4) was much higher than that of time window (5); thus, it can be predicted that the heart sounds of subject X include extra heart sounds.

Further, when the type of extra heart sound was analyzed by the extra heart sound identification unit **33*f***, the extra heart sound was identified as sound III.

Example 2

In Example 2, the target was subject Y, who had been diagnosed for the presence of sound III in the heart sounds by routine examination. Heart sound signals were extracted from the signals of the following time windows (5) and (6) in the piezoelectric signal obtained while subject Y was lying on the sheet sensor, and extra heart sounds were determined based on peak time intervals detected from the amplitude variation waveform of the heart sound signals.

Figure 30:
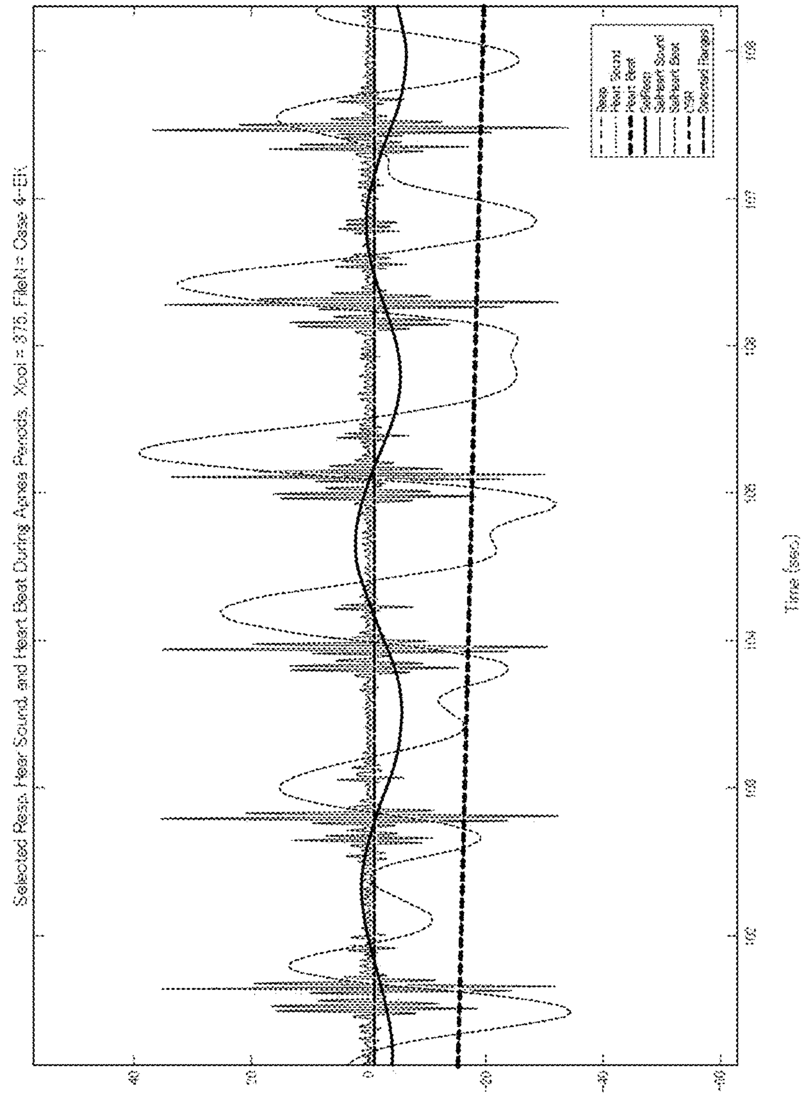
FIG. 30 shows the waveforms of heart sound signal etc. extracted from the time window of apnea in a time window with maximum CSR.
Figure 31:
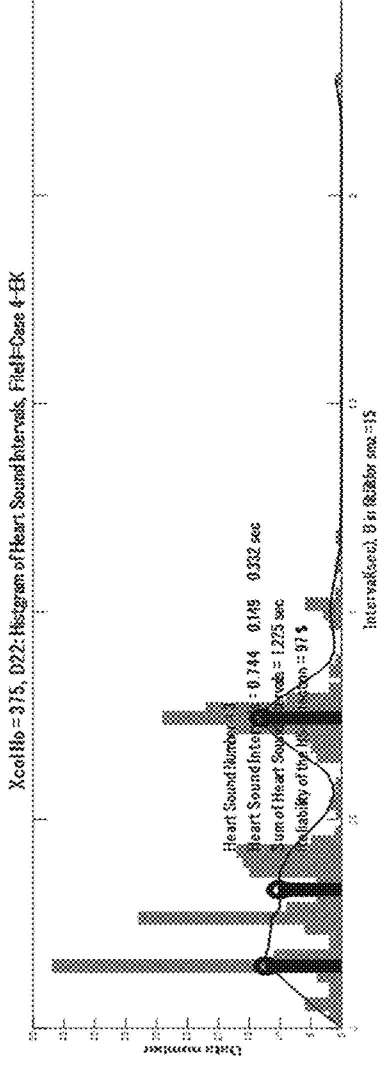
FIG. 31 shows the histogram of the distribution of peak time intervals detected from the amplitude variation waveform of the heart sound signal shown in FIG. 30.

(5) a time window of apnea in time window (2) above (6) a time window in which the SD of the heartbeat amplitude is minimum FIG. 30 shows the waveforms of the heart sound signal (black), heartbeat signal (red), CSR signal (pink), and respiratory signal (blue) extracted from time window (5). FIG. 31 shows the histogram of the distribution of peak time intervals detected from the amplitude variation waveform of the heart sound signal shown in FIG. 30.

Since the peak time intervals are roughly divided into 3 groups in FIG. 31, it can be predicted that the heart sound signals include extra heart sounds. The average time interval of each group was 0.149 sec, 0.332 sec, and 0.744 sec, and their total value (predicted heartbeat cycle) was 1.225 sec, whereas the average RR interval was 1.185 sec. Therefore, the prediction reliability was 1.185/1.225=97%.

Figure 32:
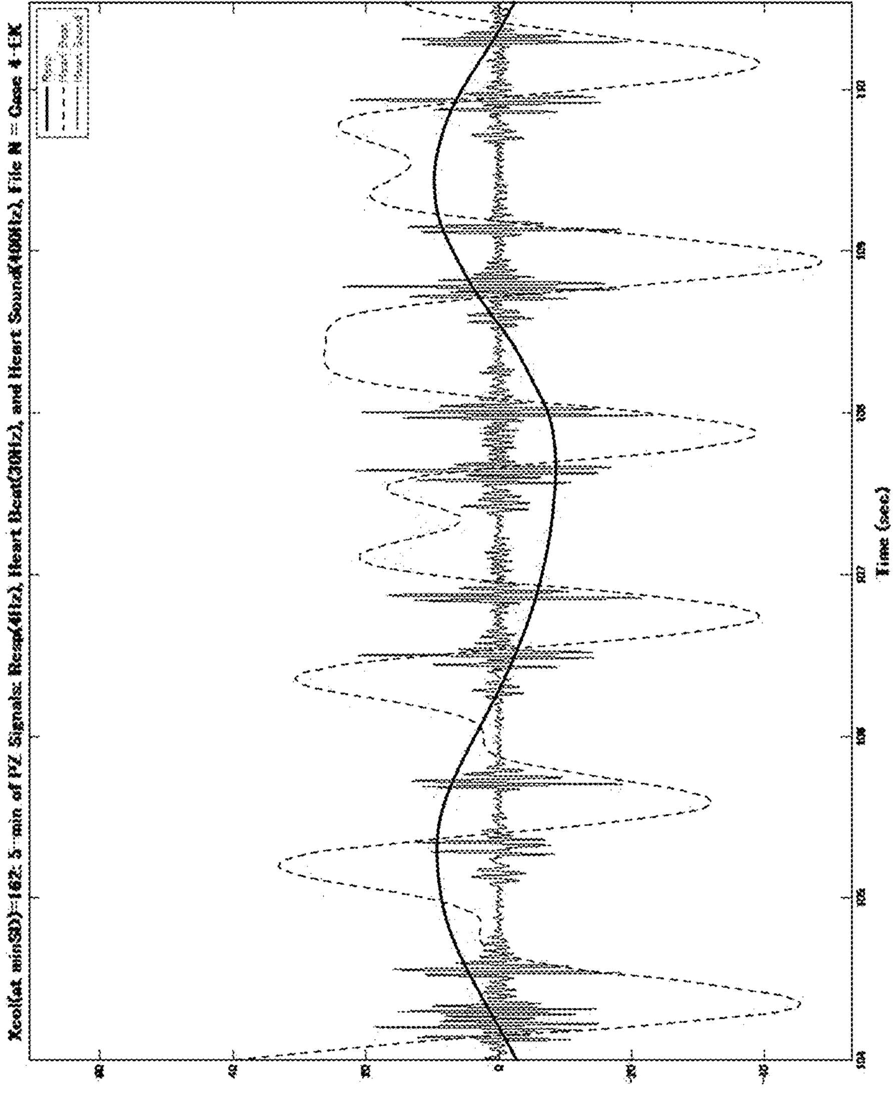
FIG. 32 shows the waveforms of heart sound signal etc. extracted from a time window in which the SD of the heartbeat amplitude is minimum.

FIG. 32 shows the waveforms of the heart sound signal (black), heartbeat signal (red), and respiratory signal (blue) extracted from time window (6). FIG. 33 shows the histogram of the distribution of peak time intervals detected from the amplitude variation waveform of the heart sound signal shown in FIG. 32.

Since the peak time intervals are roughly divided into 3 groups in FIG. 33, it can be predicted that the heart sound signals include extra heart sounds. The average time interval of each group was 0.212 sec, 0.362 sec, and 0.52 sec, and their total value (predicted heartbeat cycle) was 1.094 sec, whereas the average RR interval was 1.116 sec. Therefore, the prediction reliability was 1.094/1.116=98%.

From the above, the prediction based on the heart sound signals extracted from time windows (5) and (6) included extra heart sounds, and the prediction reliability was high in both cases. Accordingly, it can be predicted that the heart sounds of subject Y include extra heart sounds.

Further, when the type of extra heart sound was analyzed by the extra heart sound identification unit 33*f*, the extra heart sound was identified as sound IV.

REFERENCE SIGNS LIST

1. Monitoring system
2. Measuring device
21. Sheet sensor
22. Measurement unit
3. Management device (heart sound analysis device)
30. Auxiliary storage device
31. Acquisition unit
32. Heart sound extraction unit
32*a*. Respiratory signal extraction unit
32*b*. Heartbeat signal extraction unit
32*c*. Heart sound signal extraction unit
32*d*. RST analysis unit
32*e*. CSR analysis unit
32*f*. Heartbeat analysis unit
32*g*. Time window setting unit
32*h*. Heart sound signal selection unit
33. Heart sound analysis unit
33*a*. Amplitude variation waveform generation unit
33*b*. Peak detection unit
33*c*. Time interval calculation unit
33*d*. Prediction support unit
33*e*. Distribution information generation unit
33*f*. Extra heart sound identification unit
34. Display unit
4. Smartphone
D1. Heart sound extraction program
D2. Heart sound analysis program

The invention claimed is:

1. A heart sound analysis device that analyzes a heart sound signal acquired from a subject, comprising:

an amplitude variation waveform generation unit that generates an amplitude variation waveform of the heart sound signal;

a peak detection unit that detects maximum peaks in the amplitude variation waveform;

a time interval calculation unit that calculates time intervals between the maximum peaks; and a prediction support unit that supports the prediction of the state of the subject based on the time intervals, and wherein the prediction support unit comprises an extra heart sound identification unit that identifies the presence or absence of extra heart sounds in the heart sound signal and the type of extra heart sound based on the time intervals, and wherein when nth peak in the amplitude variation waveform is taken as Pn, and the time interval between (n−1) th peak Pn−1 and the nth peak Pn is taken as Sn, the extra heart sound identification unit:

searches maximum peaks that satisfy Sn−1<Sn>Sn+1, and minimum peaks that satisfy Sn−1>Sn<Sn+1, selects any maximum peak as a first peak from the searched maximum peaks, selects a minimum peak immediately following the first peak as a second peak, selects a maximum peak immediately following the second peak as a third peak, calculates a ratio of the time interval between the second and third peaks to the time interval between the first and second peaks, and determines the identification based on the ratio.

2. The heart sound analysis device according to claim 1, wherein the prediction support unit comprises a distribution information generation unit that generates distribution information indicating the distribution of the time intervals.

3. The heart sound analysis device according to claim 2, wherein the distribution information generation unit generates the distribution information in a histogram format.

4. A heart sound analysis program for making a computer work as each unit of the heart sound analysis device according to claim 1.

5. A computer-readable recoding medium that records the heart sound analysis program according to claim 4.

* * * * *